(12) United States Patent
Flynn et al.

(10) Patent No.: US 12,053,758 B2
(45) Date of Patent: Aug. 6, 2024

(54) BIODEGRADABLE HIGH-PERFORMANCE ABSORBENT POLYMERS AND METHODS THEREOF

(71) Applicant: ZYMOCHEM, INC., San Leandro, CA (US)

(72) Inventors: Allison Flynn, El Cerrito, CA (US); Harshal Akshay Chokhawala, Castro Valley, CA (US); Jonathan Carl Pistorino, Oakland, CA (US)

(73) Assignee: ZYMOCHEM, INC., San Leandro, CA (US)

( * ) Notice: Subject to any disclaimer, the term of this patent is extended or adjusted under 35 U.S.C. 154(b) by 0 days.

(21) Appl. No.: 18/331,909

(22) Filed: Jun. 8, 2023

(65) Prior Publication Data

US 2024/0181428 A1 Jun. 6, 2024

Related U.S. Application Data

(63) Continuation of application No. 17/947,022, filed on Sep. 16, 2022, now Pat. No. 11,717,805, which is a continuation of application No. PCT/US2021/034372, filed on May 26, 2021.

(60) Provisional application No. 63/030,266, filed on May 26, 2020.

(51) Int. Cl.
| | |
|---|---|
| *B01J 20/26* | (2006.01) |
| *A61L 15/26* | (2006.01) |
| *B01J 20/28* | (2006.01) |
| *C08G 63/12* | (2006.01) |
| *C08G 81/02* | (2006.01) |
| *A61L 15/60* | (2006.01) |

(52) U.S. Cl.
CPC ............ *B01J 20/267* (2013.01); *A61L 15/26* (2013.01); *B01J 20/28004* (2013.01); *B01J 20/28016* (2013.01); *C08G 63/12* (2013.01); *A61L 15/60* (2013.01)

(58) Field of Classification Search
CPC ............... B01J 20/267; B01J 20/28004; B01J 20/28016; A61L 15/26; A61L 15/60; C08G 63/12
See application file for complete search history.

(56) References Cited

U.S. PATENT DOCUMENTS

RE32,649 E * 4/1988 Brandt .................... A61F 13/53
521/149
5,965,651 A * 10/1999 Ishii ........................ C08F 8/30
524/502

(Continued)

FOREIGN PATENT DOCUMENTS

| CN | 102002234 A | 4/2011 |
| CN | 105733250 A | 7/2016 |

(Continued)

OTHER PUBLICATIONS

Ashiuchi, M. et al., Biopolymers, Wiley-VCH, 7:123 (2002).

(Continued)

*Primary Examiner* — Guy K Townsend
(74) *Attorney, Agent, or Firm* — Choate, Hall & Stewart LLP; Xiaodong Li; Alisha A. Contractor

(57) ABSTRACT

Among other things, the present disclosure provides technologies useful as super absorbent polymers.

20 Claims, 3 Drawing Sheets

(56) References Cited

U.S. PATENT DOCUMENTS

| | | | |
|---|---|---|---|
| 7,364,879 B2* | 4/2008 | Ho | C12P 19/44 435/74 |
| 7,759,088 B2* | 7/2010 | Ho | C12P 19/44 435/68.1 |
| 7,790,417 B2* | 9/2010 | Ho | C12P 19/44 435/68.1 |
| 8,420,567 B1* | 4/2013 | Naumann | C07D 301/00 502/402 |
| 8,487,049 B2* | 7/2013 | Tian | C08F 265/04 528/480 |
| 8,647,317 B2* | 2/2014 | Tian | C08F 230/085 502/402 |
| 8,703,443 B2* | 4/2014 | Yamamoto | A61Q 19/00 435/252.1 |
| 10,183,094 B2* | 1/2019 | Yamaguchi | A61L 15/60 |
| 10,435,557 B2* | 10/2019 | Orts | C08J 3/005 |
| 11,717,805 B2* | 8/2023 | Flynn | C08L 77/04 604/372 |
| 2005/0136516 A1* | 6/2005 | Ho | C12P 13/02 435/74 |
| 2008/0160569 A1* | 7/2008 | Ho | C12P 19/44 435/68.1 |
| 2008/0161605 A1* | 7/2008 | Ho | C12P 13/02 562/590 |
| 2009/0131255 A1* | 5/2009 | Ikeuchi | C08F 220/06 502/402 |
| 2009/0203790 A1* | 8/2009 | Yamamoto | A61P 17/16 514/561 |
| 2012/0230965 A1* | 9/2012 | Sung | C12N 1/20 424/93.46 |
| 2018/0273746 A1* | 9/2018 | Orts | C08L 67/04 |
| 2018/0311401 A1* | 11/2018 | Yamaguchi | C08L 1/26 |
| 2020/0095386 A1* | 3/2020 | Minty | C09D 11/04 |
| 2022/0347655 A1* | 11/2022 | Chao | C08J 3/12 |
| 2023/0058841 A1* | 2/2023 | Flynn | C08G 69/48 |

FOREIGN PATENT DOCUMENTS

| | | | | |
|---|---|---|---|---|
| CN | 106730029 A | * | 5/2017 | A61L 27/18 |
| JP | 6-322358 B2 | | 5/2018 | |
| WO | WO-2007/034795 A1 | | 3/2007 | |
| WO | WO-2009/157595 A1 | | 12/2009 | |
| WO | WO-2021/067693 A1 | | 4/2021 | |
| WO | WO-2021/242936 A1 | | 12/2021 | |

OTHER PUBLICATIONS

Ashiuchi, M., et al., A Poly-v-glutamate synthetic system of Bacillus subtilis IFO 3336: Gene cloning and Biochemical Analysis of Poly-v-glutamate produced by *Escherichia coli* Clone cells, Biochemical and Biophysical Research Communications, 263(1):6-12, (1999).

Ashiuchi, M., et al., Enzymatic Synthesis of High-Molecular-Mass Poly-v-Glutamate and Regulation of its stereochemistry, Applied and Environmental Microbiology, 70:(7)4249-4255, (2004).

International Search Report for PCT/US21/34372, 4 pages, (mailed Aug. 25, 2021).

Park, C. et al., Synthesis of super-high-molecular-weight poly-v-glutamic acid by *Bacillus subtilis* subsp. chungkookjang, Journal of Molecular Catalysis B: Enzymatic, 35:128-133, (2005).

Some, D. et al., Characterization of Proteins by Size-Exclusion Chromatography Coupled to Multi-Angle Light Scattering (SEC-MALS), Journal of Visual Experiments, 148:(e59615):1-9, (2019), doi:10.3791/59615.

Written Opinion for PCT/US21/34372, 6 pages, (mailed Aug. 25, 2021).

* cited by examiner

BIODEGRADABLE HIGH-PERFORMANCE ABSORBENT POLYMERS AND METHODS THEREOF

CROSS-REFERENCE TO RELATED APPLICATION

This application claims priority to U.S. Provisional Application No. 63/030,266, filed May 26, 2020, the entirety of which is incorporated herein by reference.

FIELD OF THE INVENTION

This disclosure relates generally to compositions of biodegradable high-performance absorbents and methods of their production and use.

SUMMARY

The present invention relates to, among other things, high-performance absorbent polymers, e.g., various PGA polymers as described herein. In some embodiments, the present disclosure provides a range of bio-based, biodegradable, γ-polyglutamic acid (γ-PGA) based crosslinked polymers with properties such as Free swell capacity, Centrifugal Retention Capacity, Absorption Under Load, Saline Flow Conductivity and/or others suitable for use in various applications, e.g., hygiene applications (e.g., diapers, tampons, etc.), and as liquid absorbents for use in medical care, construction, civil engineering, building, food, agriculture, etc.

Relative to their own mass, high-performance absorbent polymers (may also be referred to as super absorbent polymers (SAPs)) can absorb and retain a large amounts of a liquid (e.g., water, aqueous solutions). For example, applications in baby diapers, adult incontinence products, and female hygiene products comprises some of the largest end-use for SAPs. Traditionally, SAPs utilized in these applications were made of partially neutralized poly(acrylic acid) [PAA] and/or poly(acrylamide) [PAM] chains that are crosslinked using a variety of different crosslinkers. Despite their broad use, SAPs based on these crosslinked polymers have a multitude of issues including but not limited to [1] sustainability concerns surrounding the production processes of petroleum-based polymers (e.g. contributes to greenhouse emissions due to its high content of fossil-derived carbon; takes hundreds of thousands of years to form naturally and only a short time to consume); [2] toxicity concerns stemming from acrylamide from PAA-based SAP products; [3] lack of biodegradability of the SAP results in poor end-of-life properties of these products, resulting in the need for disposal via incineration or landfilling. The scale of these problems within is immense: consumption in the US alone equates to ~30 billion disposable diapers/yr.

These issues have led the industry towards certain bio-based and/or biodegradable alternatives to fossil-based SAPs. Specific properties of SAPs that are of interest, especially for hygiene applications include saline absorption (also called free swell capacity), Centrifugal retention capacity (CRC), Absorption Under Load (AUL), gel flow permeability (GFP), and vortex speed (measure rate of absorption). Bio-based and/or biodegradable alternatives developed prior to the present invention, such as cellulose- and/or starch-based polymers, however, often suffer from multiple drawbacks for industrial uses: for example, many have not been manufactured at industrial scale, reported processes for many can be very high (e.g., PGAs crosslinked with high levels of carbodiimide and/or N-hydroxysuccinic acid imide, gamma-irradiation, etc.) certain and/or many (e.g., starch-based materials) exhibit major issues with functionality and/or performance including poor fluid retention (CRC), inadequate absorption under load (AUL), undesired color and odor, and/or exuding 'slime' when over-saturated with fluids. For example, a previous commercialized starch-based SAP (Lysorb-220, AUL=6 g/g and CRC=17 g/g) displayed poor AUL and CRC when compared to PAA based SAPs.

Properties of certain commercial, fossil fuel based SAPs are described in the Table 1 below.

TABLE 1

| | | Nonwoven Standard Protocol (NWSP) Properties of Certain Fossil Fuel Based SAPs | | | | |
|---|---|---|---|---|---|---|
| Product Name | Features | Centrifuge Retention Capacity*[1] (g/g) | Absorption Under Pressure*[2] (0.7 psi, g/g) | Absorption Speed*[3] (sec) | Liquid Permeability*[4] (ml/min) | Mass Median Diameter (μm) |
| Im-930NP | High Permeability | 29 | 21 | 31 | 60 | 410 |
| SG-N21 | Balanced High Permeability | 31 | 22 | 31 | 20 | 410 |
| SQ-N158 | Balanced Fast-Absorption | 33 | 18 | 27 | 10 | 410 |
| SG-N27 | Balanced High Absorbency | 36 | 14 | 35 | 10 | 410 |
| SG-N17 | High Absorbency | 38 | 11 | 35 | 1 | 410 |

*[1]NWSP 241.3;
*[2]NWSP 242.3;
*[3]Vortex;
*[4]Measured with 0.9 wt % physiological saline under 0.3 psi Among other things, the present disclosure encompasses the recognition of these challenges, and provides polymer compositions and products thereof that address such challenges. For example, in some embodiments, the present disclosure provides PGA polymers that have comparable properties compared to commercially manufactured and utilized SAPs, e.g., PAA/PAM polymers utilized in hygiene products such as diapers. In some embodiments, provided PGA polymers are crosslinked, and possess suitable properties such as biodegradability, molecular weights, free swelling capacity, SFC (ability of swollen polymer to let liquid flow through), strength, AULs, CRCs, absorption rate, and/or GFP, for industrial use, particularly for use in hygiene products. In some embodiments, the present disclosure provides technologies for manufacturing such PGA polymers. Among other things, provided manufacturing technologies utilizes low cost and/or low levels of materials (e.g., crosslinkers) and/or do not require high cost facilities (e.g., those for gamma radiation), can provide polymer preparations at low cost compared to many prior technologies for preparing prior polymers. In some embodiments, the present disclosure provides manufactured products/articles (e.g., hygiene products such as diapers) comprising provided PGA polymers.

DETAILED DESCRIPTION OF CERTAIN DEFINITIONS

Figure 1:
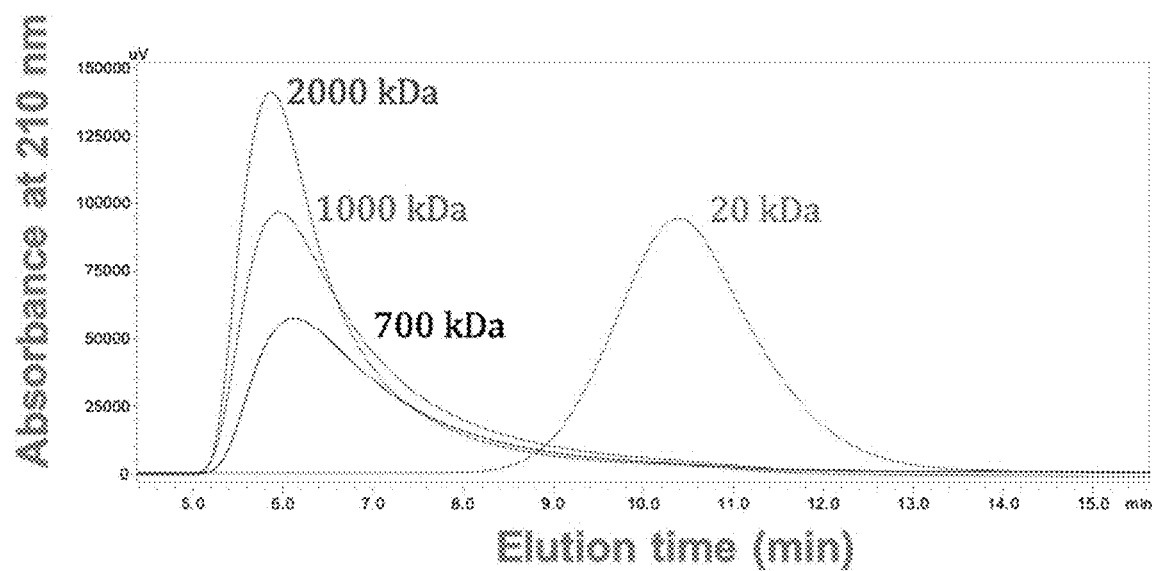
FIG. 1. SEC determination of molecular weight of polymers. Shown are traces of various γ-PGA samples.

To illustrate one or more aspects of the provided technologies, certain embodiments are described herein as examples.

In the present disclosure, unless indicated otherwise, "a," "an," "the," "at least one", and "one or more" indicate that at least one of the item is present; a plurality of such items may be present unless the context clearly indicates otherwise. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range. The terms "comprises," "comprising," "including," and "having," are inclusive and therefore specify the presence of stated features, integers, steps, operations, elements, or components, but do not preclude the presence or addition of one or more other features, integers, steps, operations, elements, components, or groups thereof. As used in this specification, the term "or" includes any and all combinations of one or more of the associated listed items.

The term γ-PGA refers to a polymer of the amino acid glutamic acid (GA). Gamma PGA, Poly-γ-glutamic acid, γ-PGA are herein used interchangeably. The term "crosslink" refers to a covalent bond between polymer chains or to the formation of such a covalent crosslink bond between polymer chains. The covalent bonds can be formed between various atoms, such as carbon, nitrogen, oxygen, sulfur, etc. In some embodiments, such atoms are in groups such as hydroxyl, thiol, amino, carboxyl, ester, ether, amide, imide, sulfide, etc. Crosslinkers generally refer to agents that can form crosslinking bonds between polymer chains. The term "aqueous system" refers to an aqueous medium optionally comprising one or more solutes or dispersed species. The aqueous system may be the aqueous phase of a multi-phase composition such as a water-in-oil emulsion. Weight by mass percentages (% weight by mass or wt % or % wt) are calculated as 100 times grams per gram (100 times gig). Saline, when used herein is an aqueous solution of sodium chloride. When used in examples, it is typically a 0.9 g/L solution of sodium chloride in deionized water.

Crosslinked PGA particles can be prepared in acidic form or in salt form, neutralized with a cationic species (wherein the amino acid carboxylic; acid side groups are deprotonated and in anionic form). Examples of suitable cationic species include, but are not limited to, $K^+$, $Na^+$, $Ca^{2+}$, and $Mg^{3+}$. In acidic forms, crosslinked PGA particles will generally have a low degree of swelling, but can be readily dispersed in water.

E-beam is a term used to denote electron beam irradiation. E-beam uses electron beam accelerators to irradiate products (with high energy electrons or beta particles). While not as harsh as gamma, E-beam cannot penetrate density of materials that gamma can. Hydrogel typically refers to a material that is absorbent but does not solubilize into solution. Absorbent is defined as the diffusion of water into a material, and in this case a polymer. A superabsorbent can absorb and retain large amounts of a liquid (e.g., from about 20, about 50, about 100, about 200, about 300 to up to about 5000 or more times) relative to its own mass.

Various technologies are available for assessing polymers in accordance with the present disclosure. Certain useful technologies are described below.

Saline Absorption or Free Swell Capacity in Saline Solution

In some embodiments, a useful protocol is similar to protocol detailed in ISO 17190-5:2001(E). Briefly, a dry absorbent powder, between 25-50 mg, is placed in a heat sealable non-woven bag [measure empty bag weight ($W_{abe}$), bag weight with the absorbent powder ($W_{ab}$), & measure control bag weight ($W_e$)] and immersed in 1 L beaker completely full with saline solution (0.9% (i.e. 9 g/L) sodium chloride in de-ionized water). After 30 minutes the bag is removed from saline solution and allowed to drain for 5 minutes fully suspended to allow any free moisture to drain. After 5 minutes the saturated bags are weighed [(measure control bag weight (Wen) and bag weight with the absorbent powder ($W_{abh}$)] and the saline absorption calculated.

Saline absorption (g of saline absorbed/g of absorbent) is calculated as follows:

$$(W_{abh} - W_{ab} - (W_{eh} - W_e))/(W_{ab} - W_{abe})$$

wherein $W_{abe}$=non-woven bag weight without the absorbent powder $W_{ab}$=non woven bag weight with the absorbent powder $W_{abh}$=non-woven bag weight containing the absorbent powder after immersion in saline $W_e$=non-woven bag weight of the control $W_{eh}$=non-woven bag weight of the control after immersion in saline Centrifugal Retention Capacity This protocol is similar to protocol detailed in ISO 17190-6:2001(E). Briefly, a dry absorbent powder, between 25-50 mg, is placed in a heat sealable non-woven bag (measure empty bag weight; $W_{abe}$ & bag weight with the absorbent powder; $W_{ab}$) and immersed in 1 L beaker completely full with saline solution (0.9% (i.e. 9 g/L) sodium chloride in de-ionized water). After 30 mins, the non woven bag is taken out of the beaker and placed in centrifuge basket (centrifuge equipped with a basket rotor). For proper balancing bags containing samples and controls are opposite to each other. Run the centrifuge to achieve 250 g centrifugal acceleration and sustain that for 3 minutes. Switch off the centrifuge, and remove the bags after the centrifuge comes to a stop. After this, the weight of the bag is recorded ($W_{abh}$). Similar procedure is also performed with empty bag ($W_e$ and $W_{eh}$ correspond to weight of bag before and after immersion in water respectively). CRC (g of saline absorbed/g of absorbent) is calculated as follows:

$$(W_{abh}-W_{ab}-(W_{eh}-W_e))/(W_{ab}-W_{abe})$$

Absorption Under Load (AUL)

For the polymers of Examples and Comparative Examples, absorbency under load was measured according to EDANA method WSP 242.2 and ISO 17190-7. Specifically, a polymer is sieved to between 30 and 60 mesh size. 0.90 g, (A) of polymer is uniformly distributed on the AUL cylinder apparatus; the plunger with weight of 0.3 or 0.7 or 0.9 psi put thereon and the weight of the entire apparatus was measured (B). The apparatus was placed into (0.9% (i.e. 9 g/L) sodium chloride in de-ionized water), and allowed to sit in the solution for 60 minutes. After 60 minutes, the apparatus was taken out and the weight was again measured (C). Using the obtained masses, AUL (g/g) was calculated according to the following formula: AUL (g/g)=(C−B)/A [Formula 2]. In the Equation, A is the weight of absorbent polymer (g), B is the weight of the AUL assembly after absorbent polymer is added, C is the weight of the AUL assembly after swelling for 60 minutes in a saline solution.

Saline Flow Conductivity

Saline flow conductivity (SFC) can be used to show how well SAP materials move liquid through a medium such as diaper fibers. In some embodiments, it is utilized as the measurement of the permeability of a gel layer formed in an aqueous-liquid-absorbing agent which has absorbed the physiological saline solution under load and is thereby swollen. Using Darcy's law and the stationary-flow method (e.g. refer to "Absorbency", edited by K. Chatterjee, Elsevier 1985, pp. 42-43 and Chemical Engineering, Vol. II, 3rd edition, J. M. Coulson and J. F. Richarson, Pergamon Press, 1978, pp. 125-127) the test measures the flow rate of saline that passes through a saturated core SAP sample that is under load. Herein saline is 0.9% (i.e. 9 g/L) sodium chloride in de-ionized water. The saline flow conductivity can be measured in accordance with the method disclosed in, e.g., paragraphs to of Column 16 of U.S. patent application publication No. 2009-0131255 and US patent number U.S. Pat. No. 8,420,567B1.

Absorption Rate (Also Called FSR: Free Swell Rate)

The free swell rate (FSR) can be utilized to indicate the profile of swelling capacity versus time of an absorbent sample. In some embodiments, it is obtained by performing free-swell capacity measurements as described above at consecutive time intervals.

Vortex Method (Absorption Speed)

The vortex method is a rapid and simple way to evaluate the SAP absorption speed. Saline solution (50 mL of 9 g/L sodium chloride in de-ionized water) is poured in a 100 mL beaker and its temperature is adjusted at 25° C. It is stirred at 600 rpm using a magnetic stirrer (stirrer bar length 400 mm). The bottom of the vortex should be near the top of the stir bar. While the saline solution is being stirred, quickly pour the superabsorbent material (2 grams) to be tested into the saline solution and start the stopwatch. The superabsorbent material to be tested should be added to the saline solution between the center of the vortex and the side of the beaker. Stop the stopwatch when the surface of the saline solution becomes flat and record the time. The time, recorded in seconds, is reported as the absorption speed.

Molecular Weight

Molecular weight may be assessed by a number of technologies in accordance with the present disclosure. In some embodiments, a molecular weight of the present disclosure is measured using a technology described below. In some embodiments, the present disclosure provides PGA polymers having various molecular weights, e.g., about 0.5 MM or more, about 0.6 MM or more, about 0.7 MM or more, about 0.8 MM or more, about 0.9 MM or more, about 1 MM or more, about 1.5 MM or more, measured using a method described below. In some embodiments, PGA polymers are crosslinked. As demonstrated in the examples, various provided polymer compositions demonstrate suitable properties, in many instances comparable to or better than those commercially utilized for, e.g., hygiene products such as diapers.

Intrinsic Viscosity

Intrinsic viscosity determination of molecular weight is dependent on that polymers increase the viscosity of a solvent in which they are dissolved. This increase allows for a convenient method of determining the molecular weight of polymers. A viscosity method is often calibrated by standards of known molecular weight with narrow molecular weight distributions. The intrinsic viscosity measured in a specific solvent is related to the molecular weight (M), by the Mark-Houwink equation.

$$[\eta]KM^a$$

where K and a are Mark-Houwink constants that depend upon the type of polymer, solvent, and the temperature of the viscosity determinations. The exponent 'a' is a function of polymer geometry, and varies from 0.5 to 2.0. The values of the Mark-Houwink parameters a and K, depend on the particular polymer-solvent system. For solvents, a value of a=0.8 is indicative of a theta solvent. A value of a=0.8 is typical of a good solvent. For most flexible polymers, 0.5<a<0.8. For semi flexible polymers, a>0.8. Rigid rod polymers typically have a=2.0.

These constants can be determined experimentally by measuring the intrinsic viscosities of several polymer samples for which the molecular weight has been determined by an independent method (i.e. osmotic pressure or light scattering). Using the polymer standards, a plot of the log [η] vs log M usually gives a straight line. The slope of this line is the "a" value and the Y-intercept is equal to the log of the "K" value.

In size-exclusion chromatography, such as gel permeation chromatography, the intrinsic viscosity of a polymer is directly related to the elution volume of the polymer. Therefore, by running several monodisperse samples of polymer in a gel permeation chromatograph (GPC), the values of K and a can be determined graphically using a line of best fit. Then the molecular weight and intrinsic viscosity relationship is defined.

Also, the molecular weights of two different polymers in a particular solvent can be related using the Mark-Houwink equation when the polymer-solvent systems have the same intrinsic viscosity. Knowing the Mark-Houwink parameters and the molecular weight of one of the polymers allows one to find the molecular weight of the other polymer using a GPC. The GPC sorts the polymer chains by volume and as intrinsic viscosity is related to the volume of the polymer chain, the GPC data is the same for the two different polymers. For example, if the GPC calibration curve is known for polystyrene in toluene, polyethylene in toluene can be run in a GPC and the molecular weight of polyethylene can be found according to the polystyrene calibration curve via the above equation.

Gel Permeation Chromatography (GPC)

Gel permeation chromatography (GPC) is a commonly used method for determining the molecular mass of polymers including PGA. GPC uses a range of mobile phases and calibrates against standards of diverse molecular masses (Birrer et al., 1994). Parameters including number-averaged molecular mass (Mn), weight-averaged molecular mass (Mw) and polydispersity (Mw/Mn) are measured as a function of elution time and comparison to standards. Experimentally, PGA solution is injected into the GPC. PGA is detected using a refractometer to give a typical chromatogram for molecular-size distribution and elution time. Apparent molecular size is estimated typically using polyethylene oxide as an approximate standard marker.

An exemplary description of measuring MW is descried below: The concentration and molecular weight of γ-PGA are determined by a GPC (gel permeation chromatography) method. Briefly, the quantitative analysis of γ-PGA is carried out by high performance liquid chromatography (Agilent, USA) using a TSK Gel G6000 PWXL gel permeation chromatogram column (7.8 mm×300 mm, Tosoh, Tokyo, Japan). The samples are eluted with a mixture of 25 mmol L-1 sodium sulfate solution:acetonitrile (8:1) at a flow rate of 0.5 mL/min and detected at 220 nm. The γ-PGA concentration is calculated by the peak area standard curve, and the molecular weight of γ-PGA was estimated according to the retention time.

HPLC (SEC)

HPLC, such as size-exclusion chromatography (SEC) is another commonly used technology for measuring molecular weight of polymers. It typically utilizes on the elution volume of an analyte to estimate molecular weight. Size exclusion chromatography allows for the separation of molecules based on the apparent size of the molecule. In some embodiments, this is important, especially for γ-PGA, which is known to have several conformations under a variety of conditions. For example, γ-PGA has several intramolecular and intermolecular interactions that contribute to the apparent size of its molecule in an aqueous environment. In some embodiments, conditions to improve γ-PGA detection comprise a dilute solution of slightly acidic γ-PGA, which could allow for appropriate separation and linearization of molecules within the solution in order to allow for improved detection.

Detailed in example 1 is the implementation of this method to determine the MW of γ-PGA. It is important to note that when the protein is not globular or undergoes non-ideal column interactions, the calibration curve based on protein standards is invalid, and the molecular weight determined from elution volume is incorrect but relative molecular weight determination remains.

SEC-MALS

In some embodiments, multi-angle light scattering (MALS) is an absolute technique that determines the molecular weight of an analyte in solution from basic physical equations. In some embodiments, a combination of SEC for separation with MALS for analysis constitutes a versatile, reliable means for characterizing solutions of one or more molecules. Since the measurement is performed at each elution volume, SEC-MALS can determine if an eluting peak is homogeneous or heterogeneous and distinguish between a fixed molecular weight distribution versus dynamic equilibrium. This protocol for SEC-MALS analyzes the molecular weight and size of pure protein monomers and aggregates. An exemplary description of measuring MW is descried below: https://www.jove.com/video/59615/characterization-proteins-size-elusion-chromatography-coupled-to Electrophoresis In an electrophoretic assay PGA can be visualized as smeared bands on an SDS-PAGE gel by staining with basic dyes, such as methylene blue and alcian blue, which correlates to the molecular-size distribution of PGA. Size-distribution profiles can be obtained using a densitometry system. Due to its simplicity, an SDS-PAGE assay can be significantly more convenient than the GPC assay, though it may be less precise, e.g., in the analysis of PGA with a molecular size of over 2000 kDa.

An exemplary description of measuring MW is descried below: SDS-PAGE are done by Laemmli's method. Purified γ-PGA is mixed with SDS-sample buffer (2% SDS, 30% glycerol, 0.25 M Tris hydroxy aminomethane. pH 6.8) and boiled for 2 min. 10 uL of the sample solution is put on 4-15% gradient acrylamide slab gel (Daiichi Pure Chemicals Ltd., Tokyo, Japan). Appropriate molecular weight standard proteins are also loaded on to a separate lane on the gel. Electrophoresis is done at the current of 1 mA per lane for 1 hour. After that, the gel is fixed with 60% ethanol, and thoroughly washed with distilled water for the removal of SDS. After equilibration with 3% acetic acid, the gel is stained with a basic dye. Each basic dye solution was prepared by solubilizing it in 3% acetic acid at the concentration of 0.5%. The excess dye is washed out with 3% acetic acid several times to get an appropriate staining image. Comparison of the relative band position of the PGA on the gel with the band position of known molecular weight of standard proteins (used as reference) will lead to determination of the molecular weight and its distribution for PGA.

Chemical Assay

Typically, a molecule of PGA has one terminal free amino group irrespective of the linkage number and the ratio of numbers between the amino group and glutamyl residues of PGA is parallel to average molecular mass (or weight). In a useful method 1-fluoro-2,4-dinitrobenzene (FDNB) is used to convert PGA into N-dinitrophenyl (DNP)-PGA by incubation in an FDNB solution, followed by polyamide hydrolysis under acidic conditions at high temperature. The resulting DNP-glutamate and free glutamate monomers are determined by a colorimetry and an HPLC assay, respectively. Average molecular mass (or weight) of PGA is estimated using Eq. (1), where the factor 129 corresponds to the molecular mass (or weight) of one glutamyl residue.

$$\text{Average molecular mass} = 129 \times \text{Number of glutamyl residues/Number of amino groups} \qquad (Eq.1)$$

Nuclear Magnetic Spectrometry $^1$H- and $^{13}$C-NMR spectroscopy can be used to determine the homogeneity and degree of crosslinking for crosslinked PGA (e.g., through measuring esterification of PGA crosslinked by formation of ester groups) (Birrer et al., 1994; Borbely et al., 1994). Chemical shifts from resulting NMR spectra can be measured relative to known standards.

DETAILED DESCRIPTION OF CERTAIN EMBODIMENTS

Among other things, the present disclosure provides PGA polymers having various controlled properties, e.g., biodegradability, molecular weights, free swelling capacity, SFC (ability of swollen polymer to let liquid flow through), strength, AULs, CRCs, absorption rate, and/or GFP etc., which polymers are particularly useful as absorbent for certain industrial uses. In some embodiments, provided PGA polymers are particularly useful for manufacturing hygiene products such as diapers. In some embodiments, the present disclosure provides manufactured products, e.g., hygiene products such as diapers that comprise provided PGA polymers. In some embodiments, the present disclosure provides methods for manufacturing provided PGA polymers and products thereof, and various uses of provided polymers and product.

Absorbent Polymers

In some embodiments, the present disclosure provides various polymers useful as absorbent. In some embodiments, the present disclosure provides PGA polymer compositions enriched for PGA molecules of certain MW as described herein, e.g., about 0.001 MM or more.

In some embodiments, provided polymer compositions are enriched for PGA molecules having MW of about 0.001 MM (million) or more. In some embodiments, provided polymer compositions are enriched for PGA molecules having MW of about 0.01 MM or more. In some embodiments, provided polymer compositions are enriched for PGA molecules having MW of about 0.1 MM or more. In some embodiments, provided polymer compositions are enriched for PGA molecules having MW of about 0.2 MM or more. In some embodiments, provided polymer compositions are enriched for PGA molecules having MW of about 0.3 MM or more. In some embodiments, provided polymer compositions are enriched for PGA molecules having MW of about 0.4 MM or more. In some embodiments, provided polymer compositions are enriched for PGA molecules having MW of about 0.5 MM or more. In some embodiments, provided polymer compositions are enriched for PGA molecules having MW of about 0.6 MM or more. In some embodiments, provided polymer compositions are enriched for PGA molecules having MW of about 0.7 MM or more. In some embodiments, provided polymer compositions are enriched for PGA molecules having MW of about 0.8 MM or more. In some embodiments, provided polymer compositions are enriched for PGA molecules having MW of about 0.9 MM or more. In some embodiments, provided polymer compositions are enriched for PGA molecules having MW of about 1 MM or more.

In some embodiments, the present disclosure provides a PGA composition, wherein the composition comprises a plurality of PGA molecules each independently in an acid, salt, ester, or amide form, wherein PGA molecules of the plurality each independently have a molecular weight of about 0.001 MM or more. In some embodiments, the molecular weight is about 0.1 MM or more. In some embodiments, the molecular weight is about 0.2 MM or more. In some embodiments, the molecular weight is about 0.3 MM or more. In some embodiments, the molecular weight is about 0.4 MM or more. In some embodiments, the molecular weight is about 0.5 MM or more. In some embodiments, the MW is about 0.6 MM or more. In some embodiments, the MW is about 0.7 MW or more. In some embodiments, the MW is about 0.8 MW or more. In some embodiments, the MW is about 0.9 MM or more. In some embodiments, the MW is about 1 MW or more. In some embodiments, the MW is about 0.7-5 MM. In some embodiments, the MW is about 0.7-3 MM.

In various embodiments, PGA molecules having a certain MW (e.g., about 0.5 MM or more, about 0.7 MM or more, about 1.0 MM or more) and/or PGA molecules of a plurality is about or at least about 5%, 10%, 15%, 20%, 25%, 30%, 35%, 40%, 45%, 50%, 55%, 60%, 65%, 70%, 75%, 80%, 85%, 90%, 95% or more wt % of a PGA polymer composition. In various embodiments, PGA molecules having a certain MW (e.g., about 0.5 MM or more, about 0.7 MW or more, about 1.0 MM or more) and/or PGA molecules of a plurality is about 5%, 10%, 15%, 20%, 25%, 30%, 35%, 40%, 45%, 50%, 55%, 60%, 65%, 70%, 75%, 80%, 85%, 90%, 95% or more mol % of a PGA polymer composition. In some embodiments, a provided composition has a low level (e.g., less than about 5%-50%, about or less than about 5%, 10%, 15%, 20%, 25%, 30%, 35%, 40%, 45%, or 50% wt % or mol %) of PGA molecules whose molecular weight is no more than about 0.5 MM, 0.4 MM, 0.3 MM, 0.2 MM, 0.1 MM or 0.05 MM.

In some embodiments, when measured for molecular weight, a polymer (which is typically a composition of a mixture of polymer molecules having different MW) may demonstrate a molecular weight of at least 0.001 M. In some embodiments, the molecular weight is about 0.2 MM or more. In some embodiments, the molecular weight is about 0.3 MM or more. In some embodiments, the molecular weight is about 0.4 MM or more. In some embodiments, the molecular weight is about 0.5 MM or more. In some embodiments, the MW is about 0.6 MM or more. In some embodiments, the MW is about 0.7 MM or more. In some embodiments, the MW is about 0.8 MM or more. In some embodiments, the MW is about 0.9 MM or more. In some embodiments, the MW is about 1 MM or more. In some embodiments, the MW is about 0.7-5 MM. In some embodiments, the MW is about 0.7-3 MM.

Molecular weight of a polymer composition or portions thereof (e.g., PGA molecules) can be assessed by various technologies as described herein. In some embodiments, MWs of the same composition from different methods may be different. In many embodiments, MWs are assessed prior to crosslinking.

In some embodiments, a MW is or close to Mn (number average molecular weight). In some embodiments, a MW is or close to Mw (weight average molecular mass). In some embodiments, a MW is or close to Mp (molecular weight of peak maxima). In some embodiments, provided polymer compositions has a dispersity of about 1.1 to 10. In some embodiments, a dispersity is about 1.1. In some embodiments, a dispersity is about 1.2. In some embodiments, a dispersity is about 1.3. In some embodiments, a dispersity is about 1.4. In some embodiments, a dispersity is about 1.5. In some embodiments, a dispersity is about 2. In some embodiments, a dispersity is about 2.5. In some embodiments, a dispersity is about 3. In some embodiments, a dispersity is about 3.5. In some embodiments, a dispersity is about 4. In some embodiments, a dispersity is about 5. In some embodiments, a dispersity is about 7. In some embodiments, a dispersity is about 10.

In some embodiments, a PGA is α-PGA. In some embodiments, a PGA is γ-PGA. In some embodiments, a PGA comprises one or more —NH—CH(CH$_2$CH$_2$COOH)—C (O)— units (independently in acid, salt, ester or amide forms) and/or one or more —NH—CH(COOH)CH$_2$CH$_2$—C(O)— units (independently in acid, salt, ester or amide forms). In some embodiments, the present disclosure provides a PGA composition, wherein the composition comprises one or more unit independently of the structure [NH—CH(COR')CH$_2$CH$_2$CO]p- or a salt form thereof, wherein:

each p is independently about 1-100,000, each R' is independently OR or —N(R)$_2$, wherein each R is independently —H, or an optionally substituted group selected from C$_{1-10}$ aliphatic, C$_{1-10}$ heteroaliphatic having 1-5 heteroatoms independently selected from nitrogen, oxygen and sulfur C$_{6-10}$ aryl, C$_{5-10}$ heteroaryl having 1-5 heteroatoms independently selected from nitrogen, oxygen and sulfur, and C$_{3-10}$ heterocyclyl having 1-5 heteroatoms independently selected from nitrogen, oxygen and sulfur; or two R groups on a nitrogen atom are taken together to form an optionally substituted 3-10 membered ring having 0-5 heteroatoms in addition to the nitrogen atom; and wherein PGA molecules of the plurality each independently have a molecular weight of about 0.001 MM or more as described herein.

In some embodiments, p is about or at least about 10, 50, 100, 150, 200, 250, 300, 400, 500, 1000, 2000, 5000, 10000, 20000, 50000, or 100000.

In some embodiments, R' is —OR. In some embodiments, R' is —OH. In some embodiments, R' is —NH$_2$. In some embodiments, one or more —COOH independently exist in a salt form, e.g., a Na, K, Ma, Ca salt form.

In some embodiments, provided polymers, e.g., PGA, are crosslinked.

Among other things, provided polymers and compositions possess a number of properties/performance characteristics and are particularly useful for use as SAPs, e.g., in hygiene products such as diapers. In some embodiments, provided polymers and compositions display one or more or all properties/performance characteristics described below. Among other things, polymers and/or compositions are selected for such properties/characteristics, and/or are enriched for polymer molecules that display one or more or all properties/performance characteristics described below In some embodiments, provided polymers has a time of absorption that is less that about 100, 90, 80, 70, 60, or 50 second, e.g., as measured by the vortex method using saline. In some embodiments, it is less than about 90 s. In some embodiments, it is less than about 60 s. In some embodiments, it is less than about 50 s. In some embodiments, it is less than about 40 s. In some embodiments, it is less than about 30 s.

Additionally or alternatively, provided polymers and compositions can provide high AULs so that they can be effectively utilized, e.g., as SAPs, under various conditions. In some embodiments, provided polymers, compositions, preparations, etc. have an AUL about 10 or more (e.g., 10-50, about 10-40, about 12-40, about 15-40, about or at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) g/g under a pressure. In some embodiments, a pressure is 0.3 psi. In some embodiments, an AUL is about 12-40 g/g (e.g., about 12, 13, 14, 15, 16, 17, 18, 19, 20, 21, 22, 23, 24, 25, 26, 27, 28, 29, 30, 31, 32, 33, 34, 35, 36, 37, 38, 39, or 40) under 0.3 psi. In some embodiments, an AUL is about 20 or more (e.g., about 20-50, about 20-40, about or at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) g/g under 0.3 psi. In some embodiments, an AUL is about 10 or more (e.g., about 10-40, about or at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) g/g under 0.7 psi. In some embodiments, an AUL is about 15 or more (e.g., about 15-40, about or at least about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) g/g under 0.7 psi. In some embodiments, an AUL is about 10 or more (e.g., about 10-40, about 10-30, about or at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) g/g under 0.9 psi. In some embodiments, AUL is measured using saline (e.g., 0.9%, or 9 g/L saline solution). In some embodiments, AUL is measured according to ISO 17190-6. In some embodiments, AUL is measured using saline (e.g., 0.9%, or 9 g/L saline solution) according to ISO 17190-7. In some embodiments, under a comparable or identical condition, prior commercial polymers utilized in diapers (e.g., PAA) display an AUL value of about 10-25 g/g. In some embodiments, AUL is about 15 or more (e.g., 15-35, about or at least about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) g/g under 0.7 psi using saline, wherein a PAA polymer displays a value of about 11-25 g/g (in some embodiments, 17 g/g was observed by Applicant) under the same or comparable conditions. In some embodiments, provided technologies display AUL values described herein for a body fluid such as urine. In some embodiments, AUL is assessed according to ISO 17190-7 or comparable protocols.

Additionally or alternatively, provided polymers and compositions can provide high CRCs so that they can be effectively utilized, e.g., as SAPs, under various conditions. In some embodiments, provided polymers, compositions, preparations have a CRC value of about 15 or more (e.g., about 15-50, about 15-40, about or at least about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) g/g using saline under a condition described herein. In some embodiments, prior commercial polymers utilized in diapers (e.g., PAA) display a CRC value as described herein. In some embodiments, provided technologies display CRC values described herein for a body fluid such as urine. In some embodiments, CRC is assessed according to ISO 17190-6 or comparable protocols.

Additionally or alternatively, provided polymers and compositions can provide high absorption rates so that they can be effectively utilized, e.g., as SAPs, under various conditions. In some embodiments, under a condition described herein, time in a vortex assessment is no more than about 90, 80, 70, 60, 50, 40, or 30 seconds. In some embodiments, it is no more than about 90 second. In some embodiments, it is no more than about 80 s. In some embodiments, it is no more than about 70 s. In some embodiments, it is no more than about 60 s. In some embodiments, it is no more than about 50 s. In some embodiments, it is no more than about 45 s. In some embodiments, it is no more than about 35 s. In some embodiments, it is no more than about 40 s. In some embodiments, it is no more than about 30 s. In some embodiments, provided technologies display absorption rate values described herein for a body fluid such as urine.

Additionally or alternatively, provided polymers and compositions can provide high absorption capacity so that they can be effectively utilized, e.g., as SAPs, under various conditions. In some embodiments, provided polymers, compositions, preparations, etc. have a fluid absorption that is about 20 or more (e.g., about 20-60, 20-50, about or at least about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) g/g. In some embodiments, a fluid is saline (e.g., 0.9% or 9 g/L). In some embodiments, a fluid is a body fluid. In some embodiments, a fluid is urine. In some embodiments, absorption, e.g., saline absorption, is assessed according to ISO 17190-5 or comparable protocols.

Additionally or alternatively, provided polymers and compositions can provide suitable strength and/or stability so that they can be effectively utilized, e.g., as SAPs, under various conditions. In some embodiments, strength and/or stability are sufficient for utilization in hygiene products such as diapers. In some embodiments, in their reasonable commercial product life provided polymers and compositions display comparable or better strength and/or stability compared to prior polymers and compositions, e.g., PAA polymers and compositions. In some embodiments, provided polymers and compositions are substantially free of, or display significantly lower levels of, "slime" and/or "bleeding" phenomenon suffered by many starch-based SAPs.

Additionally or alternatively, provided polymers and compositions can provide high flow conductivity so that they can be effectively utilized, e.g., as SAPs, under various conditions. In some embodiments, provided polymers, compositions, preparations have a saline flow conductivity of about 10-50, e.g., about 10-40, about 10-30, about 10-20, about 10, about 15, ×$10^{-7}$ cm$^3$ sec g$^{-1}$, as determined by the saline flow conductivity (SFC) test as set forth herein.

Among other things, technologies (e.g., polymers, compositions, preparations, products, etc.) of the present disclosure provide the advantages of degradability, e.g., biodegradability, compared to many commercial SAPs such as PAA-based SAPs. In some embodiments, degradability is measured according to protocols in OECD 31-B or comparable conditions. In some embodiments, no less than about 90%, 80%, 70%, 60%, 50%, 40%, 30%, 20%, 15%, 10% or 5% of the polymers degrade over 28 days.

In some embodiments, provided technologies can be prepared from renewable materials, e.g., as determined by levels of $^{14}$C, $^{13}$C, and/or $^{14}$C/$^{13}$C isotope ratios (e.g., through ASTM D6866 methods).

In some embodiments, provided technologies (e.g., polymers, compositions, preparations, products, etc.) may be provided as various particle sizes. In some embodiments, particle sizes are about 30-1000, about 100-1000, about 200-1000, about 230-1000, about 200-900, about 200-800, about 200-700, about 200-600, e.g., about or at least about 50, 100, 150, 200, 250, 300, 400, 500, 600, 700, 800, 900, or 1000, or no more than about 500, 600, 700, 800, 900, or 1000, microns. In some embodiments, a level of particles, e.g., about 50%-95%, about 60%-95%, about 70%-95%, about 75-95%, about 80%-95%, about 85-95%, about or at least about 50%, 55%, 60%, 65%, 70%, 75%, 80%, 85%, 90%, or 95% of provided technologies are particles having a size, e.g., about 30-1000, about 100-1000, about 200-1000, about 230-1000, about 200-900, about 200-800, about 200-700, about 200-600, e.g., about or at least about 50, 100, 150, 200, 250, 300, 400, 500, 600, 700, 800, 900, or 1000, or no more than about 500, 600, 700, 800, 900, or 1000, microns. In some embodiments, about 80-95% of the composition are particles having a size of about 150 to about 600 microns. In some embodiments, about 40-80% of the composition are particles between 300 and 600 microns. In some embodiments, a percentage is weight percentage. In some embodiments, a percentage is particle number percentage. In some embodiments, sizes are measured by screening through US standard mesh screens.

In some embodiments, provided technologies (e.g., polymers, compositions, preparations, products, etc.) have low levels (e.g., less than about 5%-50%, about or less than about 5%, 10%, 15%, 20%, 25%, 30%, 35%, 40%, 45%, or 50% wt % or mol %) of certain entities. In some embodiments, a percentage is about or less than about 50% by weight and/or mole. In some embodiments, a percentage is about or less than about 40% by weight and/or mole. In some embodiments, a percentage is about or less than about 30% by weight and/or mole. In some embodiments, a percentage is about or less than about 20% by weight and/or mole. In some embodiments, a percentage is about or less than about 10% by weight and/or mole. In some embodiments, a percentage is about or less than about 5% by weight and/or mole. In some embodiments, a percentage is about or less than about 4% by weight and/or mole. In some embodiments, a percentage is about or less than about 3% by weight and/or mole. In some embodiments, a percentage is about or less than about 2% by weight and/or mole. In some embodiments, a percentage is about or less than about 1% by weight and/or mole. In some embodiments, technologies have low levels of PGA molecules whose molecular weight is no more than about 0.5 MM, 0.4 MM, 0.3 MM, 0.2 MM, 0.1 MM or 0.05 MM. In some embodiments, technologies have low levels of or is substantially free of acrylic acid and/or acrylamide components. In some embodiments, provided technologies have low levels of or is substantially free of polyacrylic acid (PAA; —[CH$_2$—CH(COR')]n- or a salt form thereof) units, wherein n is about 1-10 MM. In some embodiments, provided technologies have low levels of or is substantially free of polyacrylic acid (PAA; —[CH$_2$—CH(COR')]n- or a salt form thereof) units co-polymerized with one or more polyglutamic acid ([NH—CH(COR')CH$_2$CH$_2$—CO]p- or a salt form thereof) units, wherein each of n and p is independently about 1-10 MM. In some embodiments, provided technologies have low levels of or is substantially free of polyacrylamide (PAM; —[CH$_2$—CH(CON(R)$_2$)]m-) units, wherein m is about 1-10 MM. In some embodiments, provided technologies have low levels of or is substantially free of polyacrylamide (PAM; —[CH$_2$—CH(CON(R)$_2$)]m-) units co-polymerized with one or more polyglutamic acid ([NH—CH(COR')CH$_2$CH$_2$—CO]p- or a salt form thereof) units, wherein each of m and p is independently about 1-10 MM. In some embodiments, provided technologies have low levels of or is substantially free of polyacrylic acid-acrylamide (—[[CH$_2$—CH(COOH)]n-[CH$_2$—CH(CON(R)$_2$)]m]t- or a salt form thereof) units, wherein each of n, m and t is independently about 1-10 MM. In some embodiments, provided technologies have low levels of or is substantially free of polyacrylic acid-acrylamide (—[[CH$_2$—CH(COOH)]n-[CH$_2$—CH(CON(R)$_2$)]m]t- or a salt form thereof) units co-polymerized with one or more polyglutamic acid ([NH—CH(COR')CH$_2$CH$_2$—CO]p- or a salt form thereof) units, wherein each of m and p is independently about 1-10 MM. In some embodiments, n is about or is at least about 1, 2, 3, 4, 5, 6, 7, 8, 9, 10, 11, 12, 13, 14, 15, 16, 17, 18, 19, 20, 30, 40, 50, 60, 70, 80, 90, 100, 150, 200, 300, 400, or 500. In some embodiments, m is about or is at least about 1, 2, 3, 4, 5, 6, 7, 8, 9, 10, 11, 12, 13, 14, 15, 16, 17, 18, 19, 20, 30, 40, 50, 60, 70, 80, 90, 100, 150, 200, 300, 400, or 500. In some embodiments, t is about or is at least about 1, 2, 3, 4, 5, 6, 7, 8, 9, 10, 11, 12, 13, 14, 15, 16, 17, 18, 19, 20, 30, 40, 50, 60, 70, 80, 90, 100, 150, 200, 300, 400, or 500. In some embodiments, provided polymers, compositions, preparations, etc., have low levels of or is substantially free of polysaccharides, sugars, and/or amino acids, etc., that are typically used in culture medium (e.g., those for bacteria).

In some embodiments, the present invention relates to an absorbent based on a biodegradable polymer of γ-polyglutamic acid (γ-PGA) with CRC of about 15 g/g or higher, with AUL under 0.3 psi of about 12 g/g or higher, with AUL under 0.7 psi of about 10 g/g or higher, Vortex speed of about 90 seconds or faster, and a saline flow conductivity of about $15 \times 10^{-7}$ sec $g^{-1}$ as determined by the saline flow conductivity (SFC) test as set forth herein Manufacturing Provided polymers, compositions, preparations, etc. may be manufactured utilizing various technologies in accordance with the present disclosure. For example, in some embodiments, provided technologies comprise polymerization of glutamic acid monomeric units (e.g., as glutamic acid, or a salt, ester, or amide thereof). In some embodiments, polymerization is performed biologically, e.g., in a culture (e.g., a bacteria culture) under suitable conditions. In some embodiments, polymerization is performed in chemical reactors. In some embodiments, polymerization are performed so that it can provide preparations enriched for polymer molecules having properties and/or performance characteristics as described herein compared to a reference condition, e.g., without intentional control to enrich polymer molecules having the properties and/or performance characteristics. In some embodiments, preparations are purified. In some embodiments, preparations are enriched for polymer molecules having properties and/or performance characteristics as described herein.

In some embodiments, polymers, e.g., PGA, are prepared from microbes, e.g., bacteria. In some embodiments, microbes are or comprise one or more *Bacillus* species, which may be engineered and/or optimized for the production of polymers, compositions, and/or preparations as described herein.

In some embodiments, provided polymers, compositions, preparations, etc. are prepared from a renewable feed stock. In some embodiments, a feed stock is or comprises dextrose. In some embodiments, a feed stock is or comprises pretreated lignocellulose. In some embodiments, a feed stock is or comprises glycerol. In some embodiments, a feed stock is or comprises glutamic acid or a salt, ester or amide thereof.

In some embodiments, the present disclosure provides a method, comprising:
providing a PGA composition; and
crosslink the PGA composition with a crosslinker.

In some embodiments, a PGA composition has properties as described herein, e.g., has MW, distributions, etc. as described herein. In some embodiments, a PGA composition is a culture, e.g., a bacteria culture comprising PGA. In some embodiments, crosslinking is performed by contacting a PGA composition with a crosslinker, e.g., polyglycidyl ether, at a certain level (e.g., 0.01-10% wt). In some embodiments, contacting is performed under a suitable condition, e.g., heating (e.g., about 40-200, about 50-200, about 100-200, about 40, 50, 60, 70, 80, 90, 100, 110, 120, 130, 140, 150, 160, 170, 180, 190, or 200° C.) for a suitable period of time (e.g., about 10-2000, about 10-500, e.g., about 10, 20, 30, 60, 90, 120, 150, 180, 200, 400, 800, 1000, 2000, etc. minutes) so that PGA molecules are crosslinked as desired.

In some embodiments, particles are surface crosslinked. In some embodiments, particles of crosslinked polymers are further surface crosslinked using a crosslinking technology as described herein.

In some embodiments, a crosslinker is provided as a composition comprising a number of the same or different agents that can crosslink polymers such as PGA polymers. In some embodiments, a crosslinker is or comprises diglycidyl ether, triglycidylether, poly glycidyl ether containing 3 or more epoxy groups, or a combination thereof. In some embodiments, a crosslinker is or comprises diglycidyl ether. In some embodiments, a crosslinker is or comprises triglycidylether. In some embodiments, a crosslinker is or comprises poly glycidyl ether containing 3 or more epoxy groups. In some embodiments, a crosslinker is or comprises sorbitol polyglycdyl ether. In some embodiments, a crosslinker is or comprises ERISYS 60. In some embodiments, a crosslinker is or comprises sorbitol ERISYS 61. In some embodiments, a crosslinker is or comprises trimethylolpropane triglycidyl ether. In some embodiments, a crosslinker is or comprises glycerol diglycidyl ether.

In some embodiments, crosslinking is or comprises crosslinking by radiation, e.g., γ-radiation, e-beam radiation, etc.

In some embodiments, a PGA composition is or comprises a solution of 5 or more (e.g., about 5-150, 5-100, 10-100, 20-100, 30-100, 40-100, 50-100, about or at least about 5, 10, 15, 20, 25, 30, 35, 40, 45, 50, 55, 60, 65, 70, 75, 80, 85, 90, 95 or 100) g/L PGA at a suitable pH (e.g., about 4-7). In some embodiments, a PGA composition is or comprises a solution of 10 or more g/L PGA at a suitable pH (e.g., about 4-7). In some embodiments, a PGA composition is or comprises a solution of 50 or more g/L PGA at a suitable pH (e.g., about 4-7). In some embodiments, a PGA composition is or comprises a solution of 100 or more g/L PGA at a suitable pH (e.g., about 4-7).

In some embodiments, preparations are made into desired particle sizes through, e.g., grinding. Certain useful particle sizes and/or distributions are described herein.

Crosslinking

In some embodiments, provided polymers are crosslinked. Various technologies (e.g., reagents, conditions, etc.) may be utilized in accordance with the present disclosure to control and provide structural features, properties and/or performance characteristics as described herein.

In some embodiments, crosslinking is performed using one or more crosslinkers. In some embodiments, two or more glutamic acid units each independently of the structure of —NH—CH(COOH)CH$_2$CH$_2$C$_0$— or a salt form thereof are crosslinked with a crosslinker. In some embodiments, a crosslinker is or comprises polyglycidyl ether. In some embodiments, a crosslinker is or comprises sorbitol polyglycidyl ether. In some embodiments, a crosslinker is or comprises a diol or polyol di-or poly-glycidyl ether. In some embodiments, a crosslinker is or comprises butanediol diglycidyl ether. In some embodiments, a crosslinker is or comprises neopentyl diglycidyl ether. In some embodiments, a crosslinker is or comprises trimethylolpropane triglycidyl ether. In some embodiments, a crosslinker is or comprises glycerol diglycidyl ether.

In some embodiments, provided polymers, compositions, preparations, etc. are manufactured by direct crosslinking PGA using glycidyl ethers. In some embodiments, provided polymers, compositions, preparations, etc. are prepared in a pot, one-step crosslinking method that has flexibility for enabling tunable properties of PGA-based absorbent polymer for, e.g., hygiene (and other) desired industrial applications.

In many embodiments, for conducting the crosslinking reaction of the present disclosure, amount of the crosslinker, on the basis of the total weight of (A) PGA and (B) crosslinking agent, is less than about 10 wt % of the total mass. In some embodiments, it is about 0.01-10% by weight. In some embodiments, it is about 1-10% by weight. In some embodiments, it is about 1%. In some embodiments, it is about 2%. In some embodiments, it is about 3%. In some embodiments, it is about 4%. In some embodiments, it is about 5%. In some embodiments, it is about 6%. In some embodiments, it is about 7%. In some embodiments, it is about 8%. In some embodiments, it is about 9%. In some embodiments, it is about 10%. In some embodiments, provided technologies comprise particles, e.g., PGA particles, which are surface crosslinked. Without the intention to be limited by any theory, in some embodiments, Applicant notes that if the level of crosslinking is low (e.g., below 0.1 wt % of crosslinker), water absorbance is high, but a polymer may be partially water soluble, and may lead to high extractable polymers and limit certain uses; in some embodiments, if the level of crosslinking is high (e.g., much greater than 10 wt % of crosslinker), crosslink networks may be too tight, and hydrogels may exhibit low absorbability. In some embodiments, the present technologies provide various suitable properties and/or characteristics through methods including adjusting crosslinking levels.

In some embodiments, crosslinking of the present disclosure does not require special conditions or instruments, or otherwise involve limitations on scale and/or cost. In some embodiments, glass reactors equipped with stirrer devices or culture containers in an oil or water bath can be utilized to accomplish crosslinking.

In some embodiments, methods of the present invention may further comprise one or more or all steps of hydrating crosslinked products for swelling, removing un-crosslinked components, e.g., by filtration, and drying to obtain crosslinked products which can provide high water absorbability.

In some embodiments, a crosslinking reagent is mixed with a water solution of a polymer or a composition, e.g., γ-PGA and then placed into an oven at a suitable temperature, e.g., about 150° C. for a suitable period of time, e.g., about 1.5 hours. In some embodiment, a polymer or a composition, e.g., γ-PGA is swelled with minimal water to provide maximum swelling. The swollen product is then mixed with an alcohol such as ethanol and heated to a suitable temperature, e.g., about 70° C. for a suitable period of time, e.g., about 1 hour and then filtered and dried.

Polymers, compositions and preparations of the present disclosure are hydrogels, and can be used in any desired shapes. In some embodiments, provided polymers, compositions, preparations, etc., are hydrogels. Among other things, hydrogels can be granulated into fixed shapes or made into irregular shapes, pellets, plates, etc. Provided polymers, compositions, preparations, etc., e.g., γ-PGA, can be ground using either wet or dry milling in equipment known in the art, including but not limited to rotary, cutting and knife blade mills and grinders, mortar, disk and ball mills, and attritors.

In some embodiments, the present disclosure provides high-performance absorbent polymer particles, e.g., of crosslinked γ-PGA, that can be obtained through biobased methods or from renewable starting materials. Crosslinked polymer particle, e.g., crosslinked γ-PGA particles can be dispersed in an aqueous system wherein particles swell in an aqueous system without dissolving and acting as a super-absorbent.

In some embodiments, surprisingly, crosslinked polymer particles, e.g., crosslinked γ-PGA particles can significantly increase in performance properties including CRC and AUL, absorption speed as measured using ISO 17190 test methods or test methods reported herein when the molecular weight of polymers, e.g., γ-PGA, the base polyamino acid, is increased. It is observed that such increase can be achieved whether or not further processes such as surface crosslinking are conducted. Additionally, provided technologies can provide surprising improvements regardless of how crosslinking is conducted and/or which crosslinking agent is used. Without the intention to be bound by any theory, it is noted that at least in some instances, spaghetti-type structure afforded by high MW PGA held together by crosslinking may be crucial to provide hydrogels the necessary strength to achieve AUL metrics comparable to PAA-based SAPS. In some embodiments, polymers and compositions can be optimized through crosslinking density, crosslinker structures and/or properties, e.g., epoxy value of crosslinkers (i.e., number of epoxy groups/crosslinker). In some embodiments, structure of crosslinking agents, conditions of crosslinking, particle size distributions of absorbent, surface crosslinking, etc., may also have an effect on performance properties and may be optimized accordingly to provide desired properties and/or performance characteristics.

In some embodiments, provided polymers, compositions, preparations, etc., are water soluble. In some embodiments, provided polymers, compositions, preparations, etc., are insoluble in water. In some embodiments, provided polymers, compositions, preparations, etc., are hydrogels insoluble in water. In some embodiments, compositions of PGA, e.g., γ-PGA, and crosslinking bonds are selected to render insoluble hydrogel materials, which have a hydrophilic structure capable of swelling and holding large amounts of water in the resulting swollen three-dimensional networks of crosslinked polyamino acid in the particles. Provided compositions of the present disclosure include crosslinked γ-PGA particles that when swollen with aqueous fluids absorbs up to 1000 times its dry weight of said fluid. In various embodiments, a particle size is selected between 100 and 600 microns, however, the particle size, though important in some embodiments, is not a limitation in this regard.

γ-PGA

In some embodiments, a provided polymer, composition or preparation is or comprise γ-PGA. In some embodiments, crosslinked γ-PGA of the present disclosure comprises γ-PGA that is a linear homopolymer comprising glutamic monomer units linked at the gramma position and thus having one carboxylic acid side group per monomer. In some embodiments, a crosslinked γ-PGA is prepared using D-γ-poly(glutamate), L-γ-poly(glutamate), D,L-γ-poly(glutamate) or any combination of these. Certain PGA can be prepared or obtained commercially. In some embodiments, a PGA is of biological origin and produced from a renewable feedstock. In some embodiments, γ-PGA is produced industrially using fermentation by various *Bacillus* species. *Bacillus* strains used for γ-PGA production in some embodiments require an external supply of glutamic acid for the synthesis of γ-PGA, whereas certain species can synthesize this polymer to significant levels by utilizing the intracellular glutamate pools that are synthesized via the tricarboxylic acid (TCA) cycle (referred to as glutamate independent strains). Depending on strain chosen and conditions of fermentation, one can obtain PGA with different weighted average molecular weights. Furthermore, after fermentation, PGA can be further purified using filtration with filtration membranes with different molecular cut offs to obtain PGA with the desired molecular weight profiles. In some embodiments, PGA is produced industrially using fermentation by various *Corynebacterium* species.

In some embodiments, PGA or may have a weight average molecular weight of from about 1000 Da or from about 10,000 Da or from about 20,000 Da or from about 100,000 Da or from about 2500,000 Da or from about 500,000 Da or from about 700,000 Da or from about 1,000,000 Da or from about 1,500,000 Da or from about 2,000,000 Da or from about 5,000,000 Da up to about 10,000,000 Da or up to about 15,000,000 Da or up to about 20,000,000 Da or up to about 25,000,000 Da or up to about 30,000,000 Da. Among the specific included ranges that may be mentioned for the weight average molecular of the γ-PGA are from about 10,000 Da up to about 2,000,000 Da.

In some embodiments, molecular weights of PGA or crosslinked PGA are determined using technologies described in the Examples. In some embodiments, molecular weights are determined using Procedure B. In some embodiments, a molecular weight is from about 1000 Da or from about 10,000 Da or from about 20,000 Da or from about 100,000 Da or from about 2500,000 Da or from about 500,000 Da or from about 700,000 Da or from about 1,000,000 Da or from about 1,500,000 Da or from about 2,000,000 Da or from about 5,000,000 Da up to about 10,000,000 Da or up to about 15,000,000 Da or up to about 20,000,000 Da or up to about 25,000,000 Da or up to about 30,000,000 Da. In some embodiments, a molecular weight is $M_p$. In some embodiments, it is about 0.1-10, 0.2-10, 0.3-10, 0.1-5, 0.2-5, 0.3-5, 0.1-4, 0.2-4, 0.3-4, 0.1-3, 0.2-3, 0.3-3, 0.1-2, 0.2-2, 0.3-2, or about or at least about 0.1, 0.2, 0.3, 0.35, 0.4, 0.5, 0.6, 0.7, 0.8, 0.9, 1, 1.1, 1.2, 1.3, 1.4, 1.5, 1.6, 1.65, 1.7, 1.8, 1.9. 2, 2.5, 3, 3.5, 4, 4.5, or 5 million Da. For example, in some embodiments, it is about 0.39 million Da. In some embodiments, it is about 1.6 million Da. In some embodiments, it is about 1.65 million Da. In some embodiments, it is about 1.68 million Da. In some embodiments, it is about 1.7 million Da. In some embodiments, it is about 1.8 million Da. In some embodiments, it is about 1.9 million Da. In some embodiments, it is about 2 million Da. In some embodiments, a molecular weight is $M_n$. In some embodiments, it is about 0.01-10, 0.02-10, 0.1-10, 0.2-10, 0.3-10, 0.1-5, 0.2-5, 0.3-5, 0.1-4, 0.2-4, 0.3-4, 0.1-3, 0.2-3, 0.3-3, 0.1-2, 0.2-2, 0.3-2, 0.1-1, 0.2-1 or 0.3-1, or about or at least about 0.1, 0.2, 0.3, 0.35, 0.4, 0.5, 0.6, 0.7, 0.8, 0.9, 1, 1.1, 1.2, 1.3, 1.4, 1.5, 1.6, 1.65, 1.7, 1.8, 1.9. 2, 2.5, 3, 3.5, 4, 4.5, or 5 million Da. In some embodiments, it is about 0.2 million Da. In some embodiments, it is about 0.3 million Da. In some embodiments, it is about 0.4 million Da. In some embodiments, it is about 0.5 million Da. In some embodiments, it is about 0.6 million Da. In some embodiments, it is about 0.65 million Da. In some embodiments, it is about 0.7 million Da. In some embodiments, it is about 0.8 million Da. In some embodiments, it is about 0.9 million Da. In some embodiments, it is about 1 million Da. In some embodiments, a molecular weight is $M_w$. In some embodiments, it is about 0.1-10, 0.2-10, 0.3-10, 0.1-5, 0.2-5, 0.3-5, 0.1-4, 0.2-4, 0.3-4, 0.1-3, 0.2-3, 0.3-3, 0.1-2, 0.2-2, 0.3-2, or about or at least about 0.1, 0.2, 0.3, 0.35, 0.4, 0.5, 0.6, 0.7, 0.8, 0.9, 1, 1.1, 1.2, 1.3, 1.4, 1.5, 1.6, 1.65, 1.7, 1.8, 1.9. 2, 2.5, 3, 3.5, 4, 4.5, 5, 6, 7, 8, 9, or 10 million Da. For example, in some embodiments, it is about 0.4 million Da. In some embodiments, it is about 0.5 million Da. In some embodiments, it is about 2 million Da. In some embodiments, it is about 2.2 million Da. In some embodiments, it is about 2.5 million Da. In some embodiments, it is about 3 million Da. In some embodiments, it is about 4 million Da. In some embodiments, it is about 4.6 million Da. In some embodiments, it is about 5 million Da. In some embodiments, it is about 6 million Da. In some embodiments, it is about 7 million Da. In some embodiments, it is about 8 million Da. In some embodiments, it is about 9 million Da. In some embodiments, it is about 10 million Da.

In some embodiments, a level of PGA within a composition or preparation is above a threshold (e.g., based on area % of, e.g., UV absorption at e.g., 210 nm, RI detection, etc.). In some embodiments, a level is about or at least about 10%-95%, 10-90%, 10-80%, 10%-70%, 20%-90%, 20%-80%, 20-70%, 30%-90%, 30%-80%, 40%-90%, 40%-80%, 50%-90%, 50%-80%, 10%, 20%, 30%, 40%, 50%, 60%, 70%, 75%, 80%, 85%, or 90%. In some embodiments, a percentage is about or at least about 10%. In some embodiments, a percentage is about or at least about 20%. In some embodiments, a percentage is about or at least about 30%. In some embodiments, a percentage is about or at least about 40%. In some embodiments, a percentage is about or at least about 50%. In some embodiments, a percentage is about or at least about 60%. In some embodiments, a percentage is about or at least about 70%. In some embodiments, a percentage is about or at least about 75%. In some embodiments, a percentage is about or at least about 80%. In some embodiments, a percentage is about or at least about 85%. In some embodiments, a percentage is about or at least about 90%. In some embodiments, a threshold is about molecular weight 238 Da. In some embodiments, a threshold is about molecular weight 599 Da. In some embodiments, a threshold is about molecular weight 2,100 Da. In some embodiments, a threshold is about molecular weight 5,800 Da. In some embodiments, a threshold is about molecular weight 10,000 Da. In some embodiments, a threshold is about molecular weight 12,600 Da. In some embodiments, a threshold is about molecular weight 20,000 Da. In some embodiments, a threshold is about molecular weight 42,700 Da. In some embodiments, a threshold is about molecular weight 50,000 Da. In some embodiments, a threshold is about molecular weight 99,000 Da (e.g., the peak at around 15.8 min). In some embodiments, a threshold is about molecular weight 100,000 Da. In some embodiments, a threshold is about molecular weight 217,000 Da (e.g., the peak at around 14.5 min). In some embodiments, a threshold is about molecular weight 504,000 Da (e.g., the peak at around 13.1 min). In some embodiments, a threshold is about molecular weight 969,000 Da (e.g., the peak at around 12.3 min). In some embodiments, a molecular weight is $M_p$. In some embodiments, a preparation or composition independently satisfies two or more independent levels at two or more independent thresholds. In some embodiments, a preparation or composition independently satisfies a level as described herein independently at each of the threshold of 99,000 Da, 217,000 Da, 504,000 Da and 969,000 Da. In some embodiments, when calculating area or area %, only area before a threshold is utilized (e.g., for MW greater than a threshold (e.g., 10,000 Da, 20,000 Da, 30,000 Da, 40,000 Da, 50,000 Da, 60,000 Da, 70,000 Da, 80,000 Da or 99,000 Da, or $M_p$ of 969,000, 504,000, 217,000, 99,000, 42,700, 12,600, 5,800, 2,100, 599, or 238 Da), or elution time before a peak time of a standard (e.g., those described in Procedure B)) or a time threshold (e.g., about 15, 16, 17, 17.5, 18, 19, or 20 min when using Procedure B).

In some embodiments, PGA of the present disclosure has a polydispersity in a range from about 1-50, 1-40, 1-30, 1-20, or 1-10, or about 1, 2, 3, 4, 5, 6, 7, 8, 9, or 10. In some embodiments a PGA polydispersity is 1.01. In some embodiments a PGA polydispersity is 1.1. In some embodiments a PGA polydispersity is 1.2. In some embodiments a PGA polydispersity is 1.5. In some embodiments a PGA polydispersity is 2. In some embodiments a PGA polydispersity is 2.3. In some embodiments a PGA polydispersity is 3. In some embodiments a PGA polydispersity is 3.4. In some embodiments a PGA polydispersity is 4. In some embodiments a PGA polydispersity is 5. In some embodiments a PGA polydispersity is 6. In some embodiments a PGA polydispersity is 7. In some embodiments a PGA polydispersity is 7.7. In some embodiments a PGA polydispersity is 8. In some embodiments a PGA polydispersity is 9. In some embodiments a PGA polydispersity is 10. In some embodiments, a PGA polydispersity is 50. In some embodiments, polydispersity is measured by standard GPC calculation of $M_w/M_n$ according to instrument in Procedure B (e.g., using RI).

Crosslinkers in some embodiments, PGA polymer chains are crosslinked to one another through a covalent bond. In some embodiments, crosslinking bonds are formed between carboxylic acid side groups on PGA polymer Chains. Examples of crosslink bonds between carboxylic acid side groups include, but are not limited to, crosslink bonds formed via reaction of carboxylic acid side groups with a crosslinking molecule containing two or more groups reactive with carboxyl groups such as epoxide or aziridine groups, crosslink bonds formed via reaction of carboxylic acid side groups with a carbodiimide compound to form an O-acylisourea intermediate that subsequently reacts with a crosslinking molecule containing two or more reactive amine groups, and crosslink bonds formed via reaction of carboxylic add side groups with a compound containing a glycidyl group and an ethylenically unsaturated group, with subsequent crosslinking via free radical or addition polymerization of the added ethylenically unsaturated group. Crosslink bonds can also be formed through random covalent bond formation between two atoms belonging two different linear PGA chains via actinic irradiation such as gamma or electron beam radiation.

Regardless of the type of crosslinking used, crosslinking can be at a ratio ranging from 1 crosslink bond per 10 glutamic acid monomer units to 1 crosslink bond per about 100,000 glutamic acid monomer units. In various embodiments, the crosslink ratio may be from 1 crosslink bond per 10 or per about 50 or per about 100 glutamic acid monomer units up to 1 crosslink bond per about 500 or per about 1000 or per about 10,000 or per about 50,000 or per about 100000 glutamic acid monomer units. Particular including ranges that may be mentioned are crosslink ratios of from 1 crosslink bond per 10 glutamic acid monomer units to 1 crosslink bond per about 10,000 glutamic acid monomer units of a linear PGA chain.

In some embodiments, a crosslinker is produced from a renewable feedstock. The present disclosure is not limited to any particular type of crosslinking.

Various crosslinking technologies (e.g., reagents, conditions, etc.) can be utilized in accordance with the present disclosure. In some embodiments, crosslinkers are selected from glycerol glycidyl, lipid derived glycidyl ethers and saccharide-based glycidyl ethers having three or more epoxy functional groups such as sorbitol polyglycidyl ether, isosorbide glycidyl ethers, pentaerythritol polyglycidyl ether, trimethylolethane triglycidyl ether, polyglycerol-3-glycidyl ether, castor oil triglycidyl ether, and a combination thereof. In some embodiments, polyfunctional epoxy monomers are selected preferably from digylcerol tetraglycidyl ether, dipentaerythritol tetraglycidyl ether, sorbitol polyglycidyl ether, polyglycerol polyglycidyl ether, and pentaerythritol polyglycidyl ether such as pentaerythritol tetraglycidyl ether. In some embodiments, monomers are or comprise hexafunctional glycidyl monomers, manatol polyglycidyl ether, and in particular sorbitol polyglycidyl ether. In some embodiments, a sorbitol polyglycidyl ether (CAS 68412-01-1) has the structure:

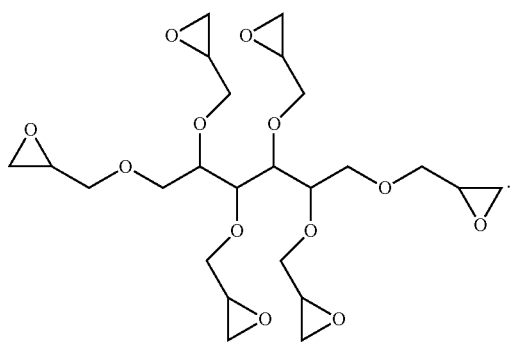 [SMILES: C(OCC(OCC1CO1)C(OCC1CO1)C(OCC1CO1)C(COCC1CO1)OCC1CO1)C1CO1]

In some embodiments, it can be purchased as Erisys® GE-60 (also referred to herein as SorbGE60) from Emerald Performance Materials as well as the water soluble Erisys® GE-61, which has three to four epoxide groups per molecule. Typically, sorbitol polyglycidyl ether (SorbGE) refers to sorbitol polyglycidyl ether wherein more than one of the sorbitol hydroxy functional groups are substituted with an epoxide functional group. It includes but is not limited to Erisys® GE-60 and Erisys® GE-61, wherein 4 and between 3 to 4 hydroxy groups are replaced with epoxy functional group, respectively.

In some embodiments, a crosslinker is or comprises a bi- or tri-functional epoxy monomer, Which is trimethylolethane triglycidyl ether, trimethylolmethane triglycidyl ether, trimethylolpropane triglycidyl ether, triphenylolmethane triglycidyl ether, trisphenol triglycidyl ether, tetraphenylol ethane triglycidyl ether, tetraglycidyl ether of tetraphenylol ethane, p-aminophenol triglycidyl ether, 1,2,6-hexanetriol triglycidyl ether, glycerol triglycidyl ether, diglycerol triglycidyl ether, glycerol ethoxylate triglycidyl ether, Castor oil triglycidyl ether, propoxylated glycerine triglycidyl ether, ethylene glycol diglycidyl ether, polyethylene glycol diglycidyl ether of molecular weights ranging from 500-10,000 Da, 1,4-butanediol diglycidyl ether, 1,6-hexanediol diglycidyl ether, neopentyl glycol diglycidyl ether, cyclohexanedimethanol diglycidyl ether, dipropylene glycol diglycidyl ether, polypropylene glycol diglycidyl ether of molecular weights ranging from 500-1,000,000 Da, dibromoneopentyl glycol diglycidyl ether, hydrogenated bisphenol A diglycidyl ether, (3,4-Epoxycyclohexane) methyl 3,4-epoxycylohexylcarboxylate or any combination thereof. In some embodiments, a suitable tri-glycidyl functional monomer is for example trimethylolpropane triglycidyl ether (CAS 30499-708) of formula

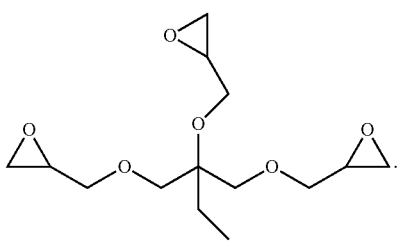 [SMILES: CCC(COCC1CO1)(COCC1CO1)OCC1CO1]

which is sold under the name Erisys® GE 30 by Emerald Performance Materials.

Cyclic and aromatic polyglycidyl ethers can also be used in accordance with the present disclosure. Examples of aromatic polyglycidyl ether compound include hydroquinone diglycidyl ether (following formula EP-1), catechol diglycidyl ether (following formula EP-2), resorcinol diglycidyl ether Phenyl]ethyl] phenyl]-2-[4-[1,1-bis [4-(2,3-epoxypropoxy) (Trade name, manufactured by Mitsubishi Chemical Corporation), resorcinol diglycidyl ether, TACTIX-742 (trade name: The EP-4), tris (4-glycidyloxyphenyl) methane DPPN-502H, DPPN-501H, and NC6000 (all trade names, manufactured by Nippon Kayaku Co., Ltd.), and DENCOL EX-201 (trade name, manufactured by Nagase ChemteX Corporation) Mower VG3101L (trade name, manufactured by Mitsui Chemicals), a compound represented by the following formula EP-6 and a compound represented by the following formula (EP-7). Novolac Di and Multi-epoxy, Diglycidyl 1,2-cyclohexanedicarboxylate, 4,4'-Methylenebis(N,N-diglycidylaniline), and 1,3,5-Triglycidyl isocyanurate can also be used as crosslinkers.

(EP-1)

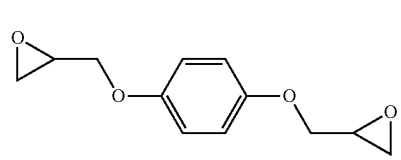

(EP-2)

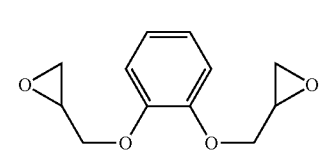

(EP-3)

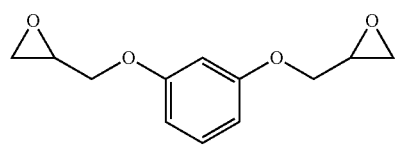

(EP-4)

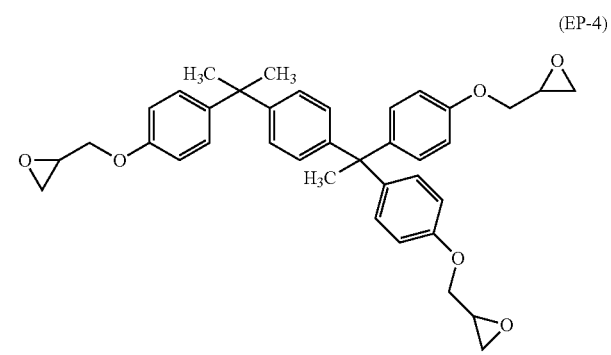

(EP-5)

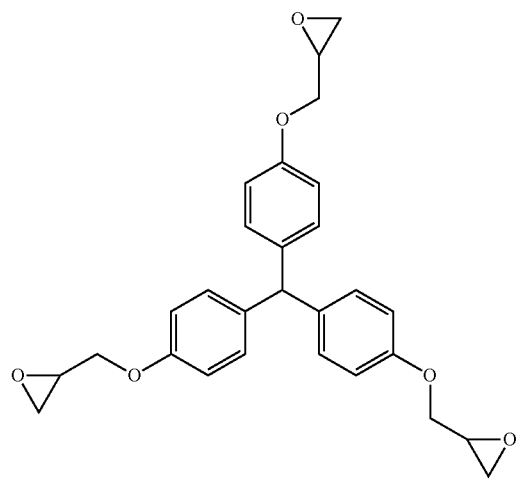

(EP-6)

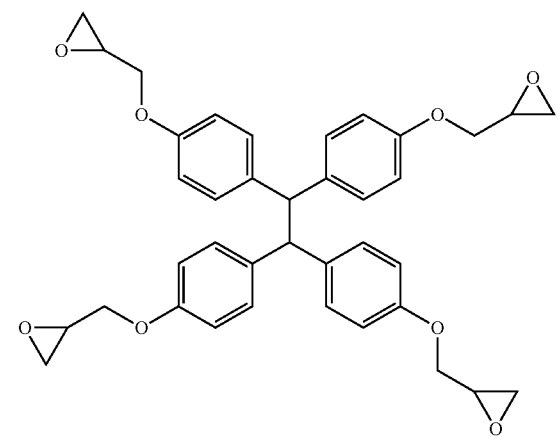

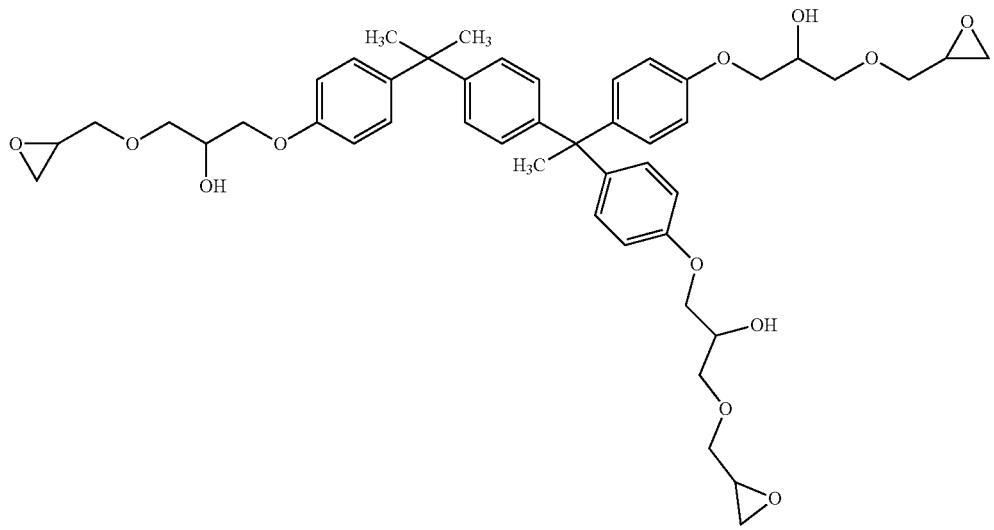

(EP-7)

Examples of suitable crosslinking molecules containing two or more reactive epoxide groups include, but are not limited to, polyglycidyl ethers of alkanepolyols and poly(alkylene glycols), including, for further example, ethylene glycol diglycidyl ether, diethylene glycol diglycidyl ether, polyethylene glycol diglycidyl ether, glycerine diglycidyl ether and triglycidyl ether, propylene glycol diglycidyl ether and butanediol diglycidyl ether. Additional suitable crosslinkers of this type include, for example, polyglycidyl ethers of erythritol, trimethylolethane, pentaerythritol, and trimethylolpropane. Further examples include diepoxyalkanes and diepoxyaralkanes, including, for further example, 1,2,3,4-diepoxybutane, 1,2,4,5-diepoxypentane, 1,2,5,6-di epoxy hexane, 1,2,7,8-di epoxy octane, 1,4- and 1,3-divinylbenzene diepoxides; polyphenol polyglycidyl ethers, including, for further example, 4,4?-isopropylidenediphenol diglycidyl ether (bisphenol A diglycidyl ether) and hydroquinone diglycidyl ether. In some embodiments, polyglycidyl ethers of alkanepolyols and poly(alkylene glycols) crosslinkers are selected, on the basis of forming biodegradable crosslink bonds and having degradation products of low toxicity.

In various embodiments, crosslinkers have three or more functional groups reactive with, e.g., carboxyl groups of PGA. In certain embodiments, it may be preferred to use a triglycidyl ether, tetraglycidyl ether, sorbitol polyglycidyl ether, or tri- or tetraaziridinyl derivative of an alkanepolyol, such as one of the examples described herein.

Crosslinking Conditions

Various crosslinking conditions, e.g., concentrations, pH, temperatures, etc. may be utilized in accordance with the present disclosure. In various embodiments, crosslinking is achieved by heating a mixture of PGA and a crosslinker in a suitable solvent, e.g., water or one comprising water, at a suitable temperature, e.g., about 40-200° C., about 100-200° C., about 1120-180° C., about 130-170° C., about 40° C., 50° C., about 60° C., about 70° C., about 80° C.; about 90° C.; about 100° C., about 110° C., about 120° C., about 130° C.; about 140° C., about 150° C., about 160° C., about 170° C., about 180° C., about 190° C., about 200° C., for a suitable period of time, e.g., about 0.5-24 hours, about 0.5-20 hours, about 0.5-15 hours, about 0.5-12 hours, about 1-5 hours, about 1-4 hours, about 0.5, 1, 1.5, 2, 2.5, 3, 3.5, 4, 4.5, 5, 5.5, 6, 6.5, 7, 7.5, 8, 8.5, 9, 9.5 or 10 hours. In some embodiments, water is removed as crosslinkers react with PGA.

In some embodiments, crosslinking is performed using one or more radiation technologies. Various such technologies are available to those skilled in the art and can be utilized in accordance with the present disclosure.

Production of Absorbent Particles:

Polymers, compositions, preparations, etc., e.g., crosslinked PGA particles can be manufactured to have desired particle sizes using variable technologies, e.g., mechanical grinding or homogenization methods, including for further example, micronization of a dried crosslinked material or homogenization of a hydrated material. In some embodiments, polymers, compositions, preparations, etc., e.g., crosslinked PGA materials, are manufactured into particles with a mean equivalent spherical diameter (that is, diameter of a sphere of equivalent volume to the mean volume of the particles) ranging from about 30 μm to 2000 μm, e.g., about 30-1000, about 30-500, about 100-2000, about 200-2000, or about 30, 50, 100, 200, 300, 400, 500, 600, 700, 800, 900, 1000, 1100, 1200, 1300, 1400, 1500, 1600, 1700, 1800, 1900, 2000 μm. In combination with technologies such as sieving a defined particle size distribution can be achieved, e.g., those described herein to provide desired properties and/or performance characteristics. Provided particles can be of various particle shape or geometry or size distributions. Examples of particle geometries include, but are not limited to, flat or round or irregular granular particles, spheres, ellipsoids, and cylindrically-shaped particles (or whiskers).

In some embodiments, provided compositions, e.g., of particles of crosslinked. γ-PGA, and processes may comprise additional additives or processes that enhance performances and/or ease of use in end applications. Examples include, but are not limited to, other molecular species that are crosslinked with polymers such as γ-PGA to alter material properties, surface crosslinking to create a protective coating and decrease or eliminate gel blocking, surfactants or emulsifiers to enhance dispersion, coating particles with active formulation ingredients, impregnating particles with active formulation ingredients, etc. The subject invention will be further described by the following examples.

Products Comprising SAPS and Uses

As described herein, in some embodiments, the present disclosure provides various products comprising provided polymers and compositions, particularly those useful as SAPs. In some embodiments, a product is or comprises a hygiene product. In some embodiments, a product is or comprise a diaper. In some embodiments, a product is or comprises a sanitary towel or napkin. In some embodiments, a product is or comprises a wound covering. In some embodiments, a product is for engineering, industrial, food, or agricultural uses.

Uses

As described herein and appreciated by those skilled in the art, provided technologies, e.g., polymers, compositions, products, etc., may be utilized for a number purposes. For example, in various embodiments, provided technologies are useful for absorbing liquid. In some embodiments, a liquid is or comprises a body fluid. In some embodiments, a body fluid is or comprises urine. In some embodiments, a body fluid is or comprises blood.

In some embodiments, the present disclosure provides the following Embodiments:

1. A polyglutamic acid (PGA) composition, wherein the composition comprises a plurality of PGA molecules each independently in its acid, salt, ester or amide form, wherein PGA molecules of the plurality each independently have a molecular weight of about 0.001 MINI or more.
2. A polyglutamic acid (PGA) composition, wherein the composition comprises a plurality of PGA molecules each independently comprising one or more unit independently of the structure:

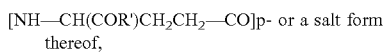
[NH—CH(COR')CH$_2$CH$_2$—CO]p- or a salt form thereof, wherein:
each p is independently about 1-100,000,
each R' is independently OR or —N(R)$_2$, wherein each R is independently —H, or an optionally substituted group selected from C$_{1-10}$ aliphatic, C$_{1-10}$ heteroaliphatic having 1-5 heteroatoms independently selected from nitrogen, oxygen and sulfur C$_{6-10}$ aryl, C$_{5-10}$ heteroaryl having 1-5 heteroatoms independently selected from nitrogen, oxygen and sulfur, and C$_{3-10}$ heterocyclyl having 1-5 heteroatoms independently selected from nitrogen, oxygen and sulfur; or two R groups on a nitrogen atom are taken together to form an optionally substituted 3-10 membered ring having 0-5 heteroatoms in addition to the nitrogen atom; and
wherein PGA molecules of the plurality each independently have a molecular weight of about 0.001 MINI or more.

3. The composition of any one of the preceding Embodiments, wherein the molecular weight is about 0.001-7 MM.
4. The composition of any one of the preceding Embodiments, wherein the molecular weight is about 0.7-5 MM.
5. The composition of any one of the preceding Embodiments, wherein the molecular weight is about 0.7-3 MM.
6. The composition of any one of the preceding Embodiments, wherein the molecular weight is about 1.0 MINI or more.
7. The composition of any one of the preceding Embodiments, wherein the molecular weight is about 1.5 MINI or more.
8. The composition of any one of the preceding Embodiments, wherein the molecular weight is about 2.0 MINI or more.
9. The composition of any one of the preceding Embodiments, wherein the molecular weight is about 1.0 MM.
10. The composition of any one of the preceding Embodiments, wherein the molecular weight is about 1.5 MM.
11. The composition of any one of the preceding Embodiments, wherein the molecular weight is about 2.0 MM.
12. The composition of any one of the preceding Embodiments, wherein the molecular weight of the composition is about 0.7-5 MM.
13. The composition of any one of the preceding Embodiments, wherein the molecular weight of the composition is about 0.7-3 MM.
14. The composition of any one of the preceding Embodiments, wherein the molecular weight of the composition is about 1.0 MM.
15. The composition of any one of the preceding Embodiments, wherein the molecular weight of the composition is about 1.5 MM.
16. The composition of any one of the preceding Embodiments, wherein the molecular weight of the composition is about 2.0 MM.
17. The composition of any one of Embodiments 12-16, wherein the molecular weight of the composition is measured by a colligative property measurement, electrophoresis, light scattering, viscometry, titration, and/or size exclusion chromatography.
18. The composition of any one of Embodiments 12-16, wherein the molecular weight of the composition is measured by light scattering.
19. The composition of any one of Embodiments 12-16, wherein the molecular weight of the composition is measured by intrinsic viscosity.
20. The composition of any one of Embodiments 12-16, wherein the molecular weight of the composition is measured by size exclusion chromatography.
21. The composition of any one of Embodiments 12-16, wherein the molecular weight of the composition is measured by gel permeation chromatography with or without coupled multi-angle light scattering (MALS).
22. The composition of any one of Embodiments 12-16, wherein the molecular weight of the composition is the number average molecular weight ($M_n$).
23. The composition of any one of Embodiments 12-16, wherein the molecular weight of the composition is the weight average molecular weight ($M_n$).
24. The composition of any one of the preceding Embodiments, wherein dispersity ($M_w/M_n$) of the PGA is about 1.1 to 10.
25. The composition of any one of the preceding Embodiments, wherein dispersity ($M_w/M_n$) of the PGA is about 2 to 10.
26. The composition of any one of the preceding Embodiments, wherein dispersity ($M_w/M_n$) of the PGA is about 2.3.
27. The composition of any one of the preceding Embodiments, wherein dispersity ($M_w/M_n$) of the PGA is about 2.4.
28. The composition of any one of the preceding Embodiments, wherein dispersity ($M_w/M_n$) of the PGA is about 7

29. The composition of any one of the preceding Embodiments, wherein the of the PGA is about 0.1-10, 0.2-10, 0.3-10, 0.1-5, 0.2-5, 0.3-5, 0.1-4, 0.2-4, 0.3-4, 0.1-3, 0.2-3, 0.3-3, 0.1-2, 0.2-2, 0.3-2, or about or at least about 0.1, 0.2, 0.3, 0.35, 0.4, 0.5, 0.6, 0.7, 0.8, 0.9, 1, 1.1, 1.2, 1.3, 1.4, 1.5, 1.6, 1.65, 1.7, 1.8, 1.9. 2, 2.5, 3, 3.5, 4, 4.5, or 5 million Da.
30. The composition of any one of the preceding Embodiments, wherein the $M_p$ is about 0.2-2 million Da.
31. The composition of any one of the preceding Embodiments, wherein the $M_p$ is about 0.3-2 million Da.
32. The composition of any one of the preceding Embodiments, wherein the $M_p$ is about 0.3-18 million Da.
33. The composition of any one of the preceding Embodiments, wherein the $M_p$ is about 0.4 million Da.
34. The composition of any one of the preceding Embodiments, wherein the $M_p$ is about 1.6 million Da.
35. The composition of any one of the preceding Embodiments, wherein the $M_p$ is about 1.7 million Da.
36. The composition of any one of the preceding Embodiments, wherein the $M_n$ of the PGA is about 0.01-10, 0.02-10, 0.1-10, 0.2-10, 0.3-10, 0.1-5, 0.2-5, 0.3-5, 0.1-4, 0.2-4, 0.3-4, 0.1-3, 0.2-3, 0.3-3, 0.1-2, 0.2-2, 0.3-2, 0.1-1, 0.2-1 or 0.3-1, or about or at least about 0.1, 0.2, 0.3, 0.35, 0.4, 0.5, 0.6, 0.7, 0.8, 0.9, 1, 1.1, 1.2, 1.3, 1.4, 1.5, 1.6, 1.65, 1.7, 1.8, 1.9. 2, 2.5, 3, 3.5, 4, 4.5, or 5 million Da.
37. The composition of any one of the preceding Embodiments, wherein the $M_n$ is about 0.02-2 million Da.
38. The composition of any one of the preceding Embodiments, wherein the $M_n$ is about 0.2-1 million Da.
39. The composition of any one of the preceding Embodiments, wherein the $M_n$ is about 0.2-0.7 million Da.
40. The composition of any one of the preceding Embodiments, wherein the $M_n$ is about 0.2 million Da.
41. The composition of any one of the preceding Embodiments, wherein the $M_n$ is about 0.6 million Da.
42. The composition of any one of the preceding Embodiments, wherein the $M_n$ is about 0.65 million Da.
43. The composition of any one of the preceding Embodiments, wherein the $M_w$ of the PGA is about 0.1-10, 0.2-10, 0.3-10, 0.1-5, 0.2-5, 0.3-5, 0.1-4, 0.2-4, 0.3-4, 0.1-3, 0.2-3, 0.3-3, 0.1-2, 0.2-2, 0.3-2, or about or at least about 0.1, 0.2, 0.3, 0.35, 0.4, 0.5, 0.6, 0.7, 0.8, 0.9, 1, 1.1, 1.2, 1.3, 1.4, 1.5, 1.6, 1.65, 1.7, 1.8, 1.9. 2, 2.5, 3, 3.5, 4, 4.5, 5, 6, 7, 8, 9, or 10 million Da.
44. The composition of any one of the preceding Embodiments, wherein the $M_w$ is about 0.4-5 million Da.
45. The composition of any one of the preceding Embodiments, wherein the $M_w$ is about 0.5-2.5 million Da.
46. The composition of any one of the preceding Embodiments, wherein the $M_w$ is about 0.5 million Da.
47. The composition of any one of the preceding Embodiments, wherein the $M_w$ is about 2.2 million Da.
48. The composition of any one of the preceding Embodiments, wherein the $M_w$ is about 4.6 million Da.
49. The composition of any one of Embodiments 24-48, wherein the molecular weight of the composition is measured by size exclusion chromatography.
50. The composition of any one of Embodiments 24-48, wherein the molecular weight of the composition is measured according to Procedure B.
51. The composition of any one of Embodiments 24-48, wherein the molecular weight of the composition is measured according to Procedure B using RI detection.
52. The composition of any one of the preceding Embodiments, wherein the molecular weight is measured before crosslinking.
53. The composition of any one of the preceding Embodiments, wherein the molecular weight is measured after crosslinking.
54. The composition of any one of the preceding Embodiments, wherein the amount of the PGA molecules of the plurality is about or at least about 10%, 20%, 30%, 40%, 50%, 60%, 70%, 80%, or 90% or more by weight.
55. The composition of any one of the preceding Embodiments, wherein the amount of the PGA molecules of the plurality is about or at least about 10%, 20%, 30%, 40%, 50%, 60%, 70%, 80%, or 90% or more by molar ratio.
56. The composition of any one of the preceding Embodiments, wherein the composition contains a substantial portion (e.g., about 30%, 40%, 50%, 60%, 70%, 80%, 90%, etc. or more) by weight of PGA molecules with a molecular weight above 0.02 MM.
57. The composition of any one of the preceding Embodiments, wherein the composition contains a substantial portion (e.g., about 30%, 40%, 50%, 60%, 70%, 80%, 90%, etc. or more) by weight of PGA molecules with a molecular weight above 0.7 M.
58. The composition of any one of the preceding Embodiments, wherein the composition contains a substantial portion (e.g., about 30%, 40%, 50%, 60%, 70%, 80%, 90%, etc. or more) by weight of PGA molecules with a molecular weight above 1 M.
59. The composition of any one of the preceding Embodiments, wherein the composition contains a substantial portion (e.g., about 30%, 40%, 50%, 60%, 70%, 80%, 90%, etc. or more) by molar ratio of PGA molecules with a molecular weight above 0.02 MM.
60. The composition of any one of the preceding Embodiments, wherein the composition contains a substantial portion (e.g., about 30%, 40%, 50%, 60%, 70%, 80%, 90%, etc. or more) by molar ratio of PGA molecules with a molecular weight above 0.7 M.
61. The composition of any one of the preceding Embodiments, wherein the composition contains a substantial portion (e.g., about 30%, 40%, 50%, 60%, 70%, 80%, 90%, etc. or more) by molar ratio of PGA molecules with a molecular weight above 1 M.
62. The composition of any one of the preceding Embodiments, wherein the composition is crosslinked.
63. The composition of any one of the preceding Embodiments, wherein two or more glutamic acid units each independently of the structure of —NH—CH(COOH) $CH_2CH_2C_0$— or a salt form thereof are crosslinked with a crosslinker.
64. The composition of Embodiment 63, wherein a crosslinker is sorbitol polyglycidyl ether.
65. The composition of Embodiment 63 or 64, wherein a crosslinker is butanediol diglycidyl ether.
66. The composition of any one of Embodiments 63-65, wherein a crosslinker is neopentyl diglycidyl ether.
67. The composition of any one of any one of the preceding Embodiments, wherein the weight percentage (wt %) of a crosslinker is about 0.01-10%.
68. The composition of any one of any one of the preceding Embodiments, wherein the weight percentage (wt %) of a crosslinker is about 1-10%.
69. The composition of Embodiments 68, wherein the weight percentage (wt %) of a crosslinker is about 1%.

70. The composition of Embodiments 68, wherein the weight percentage (wt %) of a crosslinker is about 2%.
71. The composition of Embodiments 68, wherein the weight percentage (wt %) of a crosslinker is about 4%.
72. The composition of Embodiments 68, wherein the weight percentage (wt %) of a crosslinker is about 7%.
73. The composition of Embodiments 68, wherein the weight percentage (wt %) of a crosslinker is about 10%.
74. The composition of any one of the preceding Embodiments, wherein the composition comprises PGA particles, which are surface crosslinked.
75. The composition of any one of any one of the preceding Embodiments, wherein the time of absorption is less than 90 seconds as measured by the vortex test method using saline.
76. The composition of any one of any one of the preceding Embodiments, wherein the time of absorption is less than 60 seconds as measured by the Vortex test method using saline.
77. The composition of any one of the preceding Embodiments, wherein the absorption under load (AUL) is about 12 or more (e.g., 12-40) g/g under 0.3 psi using saline.
78. The composition of any one of the preceding Embodiments, wherein the absorption under load (AUL) is about 20 or more (e.g., 20-40) g/g under 0.3 psi.
79. The composition of any one of the preceding Embodiments, wherein the absorption under load (AUL) is about 10 or more (e.g., 10-35) g/g under 0.7 psi using saline.
80. The composition of any one of the preceding Embodiments, wherein the absorption under load (AUL) is about 15 or more (e.g., 15-40) g/g under 0.7 psi.
81. The composition of any one of the preceding Embodiments, wherein the absorption under load (AUL) is about 10 or more (e.g., 10-30) g/g under 0.9 psi using saline.
82. The composition of any one of the preceding Embodiments, wherein the AUL is measured according to ISO 17190-7.
83. The composition of any one of the preceding Embodiments, wherein the absorption under load (AUL) is about 15 or more (e.g., 15-35) g/g under 0.7 psi using saline, wherein a PAA polymer displays a value of about 11-25 g/g under the same or comparable conditions.
84. The composition of any one of the preceding Embodiments, wherein the CRC of the composition is 15-50 g/g using saline.
85. The composition of any one of the preceding Embodiments, wherein the speed of absorption measured using vortex test using saline is between 30 to 60 sec.
86. The composition of any one of the preceding Embodiments, wherein the saline absorption of the composition is 20-50 g/g.
87. The composition of any one of the preceding Embodiments, wherein the composition is substantially free of slime observed for starch-based SAPs.
88. The composition of any one of the preceding Embodiments, wherein the composition is substantially free of bleeding observed for starch-based SAPs.
89. The composition of any one of the preceding Embodiments, wherein the composition possesses biodegradability.
90. The composition of any one of the preceding Embodiments, wherein when measured by OECD 301-B, no less than about 60% the polymers degrade over 28 days.
91. The composition of any one of the preceding Embodiments, wherein when measured by OECD 301-B, no less than about 80% the polymers degrade over 30 days.
92. The composition of any one of the preceding Embodiments, wherein when measured by OECD 301-B, no less than about 90% the polymers degrade over 30 days.
93. The composition of any one of the preceding Embodiments, wherein when measured by OECD 301-B, no less than about 95% the polymers degrade over 30 days.
94. The composition of any one of the preceding Embodiments, wherein when measured by OECD 301-B, time consumed to degrade a certain level of the composition is no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days longer than time consumed to degrade the same level of a positive control under a comparable condition.
95. The composition of any one of the preceding Embodiments, wherein when measured by OECD 301-B, time consumed to degrade a certain level of the composition is no more than about 10 days longer than time consumed to degrade the same level of a positive control under a comparable condition.
96. The composition of any one of the preceding Embodiments, wherein when measured by OECD 301-B, time consumed to degrade a certain level of the composition is no more than about 20 days longer than time consumed to degrade the same level of a positive control under a comparable condition.
97. The composition of any one of the preceding Embodiments, wherein when measured by OECD 301-B, time consumed to degrade a certain level of the composition is no more than about 30 days longer than time consumed to degrade the same level of a positive control under a comparable condition.
98. The composition of any one of the preceding Embodiments, wherein when measured by OECD 301-B, time consumed to degrade a certain level of the composition is shorter than time consumed to degrade the same level of a positive control under a comparable condition.
99. The composition of any one of the preceding Embodiments, wherein when measured by OECD 301-B, time consumed to degrade a certain level of the composition is about the same as time consumed to degrade the same level of a positive control under a comparable condition.
100. The composition of any one of the preceding Embodiments, herein the level is about 20%.
101. The composition of any one of Embodiments 94-100, wherein the level is about 50%.
102. The composition of any one of Embodiments 94-100, wherein the level is about 80%.
103. The composition of any one of Embodiments 94-100, wherein the level is about 90%.
104. The composition of any one of Embodiments 94-100, wherein the level is about 95%.
105. The composition of any one of Embodiments 94-100, wherein a positive control is sodium benzoate.

106. The composition of any one of the preceding Embodiments, wherein the composition has a saline flow conductivity of about $15 \times 10^{-7}$ cm$^3$ sec g$^{-1}$.
107. The composition of any one of the preceding Embodiments, wherein the composition comprises a number of particles having a size of about 30 to about 1000 microns.
108. The composition of any one of the preceding Embodiments, wherein about 80-95% of the composition by weight are particles having a size of about 150 to about 600 microns.
109. The composition of any one of the preceding Embodiments, wherein about 40-80% of the composition by weight are particles between 300 and 600 microns.
110. A method for preparing a PGA composition of any one of the preceding Embodiments, comprising polymerizing a number of glutamic units to provide a composition of any one of the preceding Embodiments.
111. A method for preparing a PGA composition of any one of the preceding Embodiments, comprising polymerizing a number of glutamic units to provide a composition of any one of Embodiments 1-61.
112. The method of any one of any one of the preceding Embodiments, wherein a PGA composition is or comprises a solution of >50 g/L PGA at pH 4-7.
113. The method of any Embodiment, wherein the PGA is prepared from microbes.
114. The method of any Embodiment, wherein the PGA is prepared from microbes, wherein the microbes are or comprise one or more *Bacillus* species.
115. The method of any one of Embodiments 113-114, wherein one or more microbes are engineered.
116. The method of any one of the preceding Embodiments, wherein the PGA composition is prepared from a renewable feed stock.
117. The method of any one of the preceding Embodiments, wherein the PGA composition is prepared from a feed stock which is or comprises dextrose.
118. The method of any one of the preceding Embodiments, wherein the PGA composition is prepared from a feed stock which is or comprises pretreated lignocellulose.
119. The method of any one of the preceding Embodiments, wherein the PGA composition is prepared from a feed stock which is or comprises glycerol.
120. The method of any one of the preceding Embodiments, wherein the PGA composition is prepared from a feed stock which is or comprises glutamic acid.
121. The method of any one of the preceding Embodiments, comprising crosslinking PGA polymers.
122. The method of any one of the preceding Embodiments, comprising crosslinking a PGA composition of any one of Embodiments 1-61 and 112-120.
123. The method of any one of the preceding Embodiments, comprising contacting the PGA composition with a crosslinker composition.
124. The method of any one of the preceding Embodiments, wherein a crosslinker composition is or comprises diglycidyl ether, triglycidylether, poly glycidyl ether containing 3 or more epoxy groups, or a combination thereof.
125. The method of any one of the preceding Embodiments, wherein a crosslinker composition is or comprises diglycidyl ether.
126. The method of any one of the preceding Embodiments, wherein a crosslinker composition is or comprises triglycidylether.
127. The method of any one of the preceding Embodiments, wherein a crosslinker composition is or comprises poly glycidyl ether containing 3 or more epoxy groups.
128. The method of any one of the preceding Embodiments, wherein a crosslinker composition is or comprises sorbitol polyglycdyl ether.
129. The method of any one of the preceding Embodiments, wherein a crosslinker composition is or comprises ERISYS 60.
130. The method of any one of the preceding Embodiments, wherein a crosslinker composition is or comprises ERISYS 61.
131. The method of any one of the preceding Embodiments, comprising contacting the PGA composition with a crosslinker of about 0.01-10% wt.
132. The method of any one of Embodiments 123-129, wherein the contacting is performed at about 150° C. for 90 min.
133. The method of any one of the preceding Embodiments, comprising crosslinking PGA polymers with radiation.
134. The method of any one of the preceding Embodiments, comprising crosslinking PGA polymers with e-beam radiation.
135. The method of any one of the preceding Embodiments, comprising crosslinking PGA polymers with γ-radiation.
136. The method of any one of the preceding Embodiments, comprising crosslinking a PGA composition of any one of Embodiments 1-61 and 112-120.
137. The method of any one of the preceding Embodiments, wherein the composition is made into certain particle sizes.
138. The method of any one of the preceding Embodiments, wherein the composition is made into certain particle sizes to provide a composition of any one of Embodiments 107-109.
139. The composition or method of any one of the Embodiments, wherein the CRC of the composition is measured using ISO 17190-6.
140. The composition or method of any one of the Embodiments, wherein the AUL of the composition is measured using ISO 17190-7.
141. The composition or method of any one of the Embodiments, wherein the saline absorption of the composition is measured using ISO 17190-5.
142. The composition or method of any one of the Embodiments, wherein the absorption speed of the composition is measured by the Vortex test.
143. The composition or method of any one of the Embodiments, wherein the PGA is γ-PGA.
144. The composition or method of any one of the Embodiments, wherein the PGA is γ-PGA from a bio-source (e.g., fermentation, microbes, culture, etc.).
145. An article comprising a composition of any one the preceding Embodiments.
146. The article of Embodiment 145, wherein the article is or comprises a diaper.
147. The article of Embodiment 145, wherein the article is or comprises a sanitary towel or napkin.
148. The article of Embodiment 145, wherein the article is or comprises a wound covering.

149. A method, comprising:
  contacting a liquid with a composition or article or any one of the preceding Embodiments,
  wherein the composition or article absorbs the liquid.
150. The method of Embodiment 149, wherein the liquid is or comprises a body fluid.
151. The method of Embodiment 149, wherein the liquid is or comprises urine, blood, and other bodily fluids.
152. The method of Embodiment 149, wherein the liquid is or comprises blood.
153. The method of Embodiment 149, wherein the liquid is or comprises urine.
154. The method of any one of the preceding Embodiments, comprising crosslinking PGA polymers with e-beam radiation at energy level 15, 30, 45, 60, 75, 90, 105, or 20 kGy.
155. The method of any one of the preceding Embodiments, wherein a crosslinker composition is or comprises resorcinol diglycidyl ether.
156. The method of any one of the preceding Embodiments, wherein a crosslinker composition is or comprises 1,3,5-Triglycidyl isocyanurate.
157. The method of any one of the preceding Embodiments, wherein a crosslinker composition is or comprises cyclic and aromatic polyglycidyl ethers.
158. The method of any one of the preceding Embodiments, wherein a crosslinker composition is or comprises trimethylolpropane triglycidyl ether.
159. The method of any one of the preceding Embodiments, wherein a crosslinker composition is or comprises polyethylene glycol diglycidyl ether.
160. The method of any one of the preceding Embodiments, wherein a crosslinker composition is or comprises polypropylene glycol diglycidyl ether.
161. The method of any one of the preceding Embodiments, wherein a crosslinker composition is or comprises ethylene glycol diglycidyl ether.
162. The method of any one of the preceding Embodiments, wherein a crosslinker composition is or comprises glycerol diglycidyl ether.

EXEMPLIFICATION

Certain non-limiting examples are provided below to illustrate one or more aspects of provided technologies.

Example 1. Provided Technologies Demonstrate Properties and Characteristics for Uses as SAPs Among other things, the present disclosure provides SAP technologies (e.g., polymers, compositions, methods, etc.). Demonstrated herein are compositions and preparations demonstrating valuable properties and/or performances for various uses including as SAPs, and technologies (reagents, conditions, etc.) for manufacturing such compositions and preparations.

Molecular Weight Determination:

In some embodiments, molecular weight was determined by HPLC using Size Exclusion Chormotography (SEC) using UV and/or RI (Refractive index) detectors. Specifically, 100 mg of γ-PGA (or another sample to be tested) was mixed into 10 mL of purified water. Samples are mixed until the γ-PGA was completely dissolved. For more viscous γ-PGA samples, this may involve allowing the tubes to gently rotate overnight. The 10 g/L solution was then passed through a sterile 0.22 um syringe filter. Serial dilutions were done to get concentrations of 5, 4, 2.5, 1, and 0.5 g/L solutions of each γ-PGA sample. 1 uL of each sample was injected into a Sepax SRT SEC-500 column (4.6×150 mm) with accompanying Sepax SRT SEC-1000 guard column (7.8×50 mm). The column was held at 30° C., and a 0.1 M potassium phosphate (pH 7) buffer was used as the mobile phase with a flow rate of 0.35 ml/min. Samples were detected at 210 nm using a LC-2030 UV Detector. Elution times for certain γ-PGA standards are shown in FIG. 1, and molecular weight was determined according to the standards (in FIG. 1, labeled molecular weights were provided by supplier).

Figure 2:
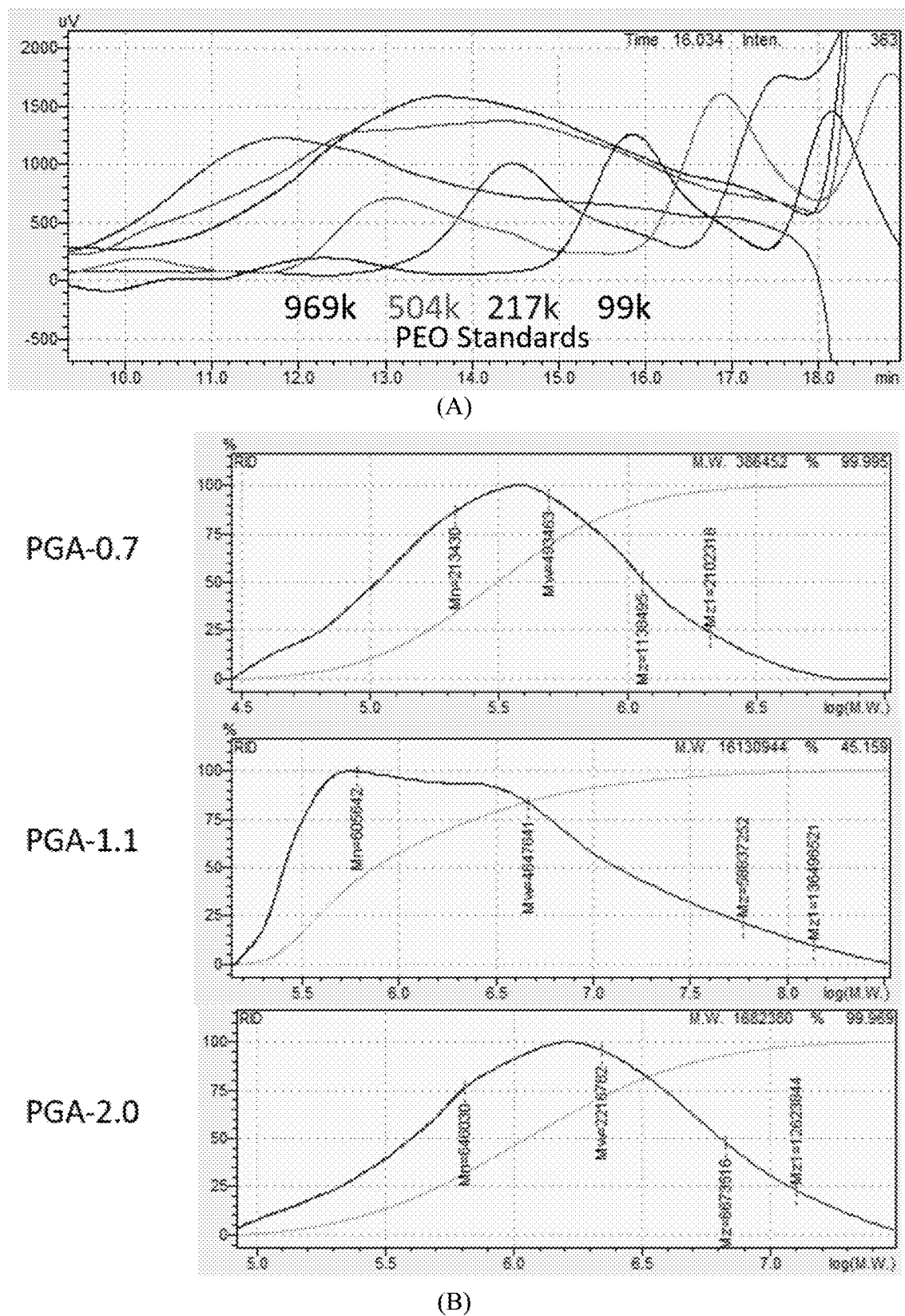
FIG. 2. Certain results using Procedure B. (A) Certain raw data. Peaks for certain standards: 969,000 Da at about 12.3 min; 504,000 Da at about 13.1 min; 217,000 Da at about 14.5 min; 99,000 Da at about 15.8 min. Peak for PGA-2.0 is about 11.8 min; peak for PGA-1.1 is about 14.3 min (higher than peak for 217,000 Da in this specific figure); and peak for PGA-0.7 is about 13.6 min. (B) Certain molecular weight results.

In another useful procedure (Procedure B), molecular weight was determined by HPLC using Size Exclusion Chormotography (SEC) using UV and/or RI (Refractive index) detectors. Specifically, 100 mg of γ-PGA (or another sample to be tested) was mixed into 10 mL of purified water. Samples are mixed until the γ-PGA was completely dissolved. For more viscous γ-PGA samples, this may involve allowing the tubes to gently rotate overnight. The 10 g/L solution was then passed through a sterile 0.22 um syringe filter. Serial dilutions were done to get concentrations of 5, 4, 2.5, 1, and 0.5 g/L solutions of each γ-PGA sample. 1 uL of each sample was injected into a Showdex SB-805 HQ. The column was held at 30° C., and a 0.05 M citrate buffer was used as the mobile phase with a flow rate of 0.5 mL/min. Samples were detected at 210 nm using a LC-2030 UV and RI Detector. Elution times for certain γ-PGA are shown in FIG. 2, and molecular weights were determined as follows using Shimadzu Lab Solutions GPC software. First, we constructed a molecular weight calibration curve by running several monodisperse samples of the polymer Poly Ethylene Oxide (PEO) with known molecular weights and measuring their retention time. Graphically a line of best fit for this calibration curve (i.e. retention time vs molecular weight) was obtained. This calibration was then applied to the γ-PGA samples run under the same conditions (e.g. shown in FIG. 2) using Shimadzu Lab Solutions GPC software to obtain various molecular weight parameters reported herein for the γ-PGA samples. γ-PGA peaks corresponding to elution times up to ~17.5 mins were considered for this analysis. For example, PEO standards from PSS Polymer Standards GmbH were utilized (Part No. PSS-speokitr1, Lot No. peokitr1sa-14) to construct molecular weight calibration curve. $M_p$ [Da] values were used to build the calibration curve from one or more or all 10 PEO standards ($M_p$ [Da]=969,000; 504,000; 217,000; 99,000; 42,700; 12,600; 5,800; 2,100; 599, 238.) Certain results were presented in FIG. 2. In some embodiments, the present disclosure provides optionally crosslinked PGA preparations (e.g., γ-PGA preparations) comprising PGAs with observed molecular weights (e.g., assessed by Procedure B; Da) of about 10,000 to 20,000,000, 20,000 to 15,000,000, 20,000 to 10,000,000, 20,000 to 5,000,000, 20,000 to 2,000,000, 20,000 to 1,000,000, 30,000 to 10,000,000, 50,000 to 10,000,000, 300,000 to 2,000,000, 100,000 to 1,000,000, 200,000 to 700,000, 400,000 to 5,000,000, etc. In some embodiments, molecular weights are $M_p$. In some embodiments, molecular weights are $M_n$. In some embodiments, molecular weights are $M_w$. See, for example, data in the Examples. In some embodiments, a signal detected (e.g., UV absorption at 210 nM, RI detection, etc.) at a time corresponding to the peak elution of a 12,600 Da standard is about or at least about 10%-95%, 10%-90%, 10-80%, 10%-70%, 20%-90%, 20%-80%, 20-70%, 30%-90%, 30%-80%, 40%-90%, 40%-80%, 50%-90%, 50%-80%, 10%, 20%, 30%, 40%, 50%, 60%, 70%, 75%, 80%, 85%, or 90% of the highest peak for a sample (e.g., in FIG. 2, for PGA-1.1, the peak at about 14.3 min). In some embodiments, a signal detected (e.g., UV absorption at 210 nM, RI detection, etc.) at a time corresponding to the peak elution of a 42,700 Da standard is about or at least about 10%-95%, 10-90%, 10-80%, 10%-70%, 20%-90%, 20%-80%, 20-70%, 30%-90%, 30%-80%, 40%-90%, 40%-80%, 50%-90%, 50%-80%, 10%, 20%, 30%, 40%, 50%, 60%, 70%, 75%, 80%, 85%, or 90% of the highest peak for a sample (e.g., in FIG. 2, for PGA-1.1, the peak at about 14.3 min). In some embodiments, a signal detected (e.g., UV absorption at 210 nM, RI detection, etc.) at a time corresponding to the peak elution of a 99,000 Da standard (e.g., in FIG. 2, the peak at about 15.8 min) is about or at least about 10%-95%, 10-90%, 10-80%, 10%-70%, 20%-90%, 20%-80%, 20-70%, 30%-90%, 30%-80%, 40%-90%, 40%-80%, 50%-90%, 50%-80%, 10%, 20%, 30%, 40%, 50%, 60%, 70%, 75%, 80%, 85%, or 90% of the highest peak for a sample (e.g., in FIG. 2, for PGA-1.1, the peak at about 14.3 min). In some embodiments, a signal detected (e.g., UV absorption at 210 nM, RI detection, etc.) at a time corresponding to the peak elution of a 217,000 Da standard (e.g., in FIG. 2, the peak at about 14.5 min) is about or at least about 10%-95%, 10-90%, 10-80%, 10%-70%, 20%-90%, 20%-80%, 20-70%, 30%-90%, 30%-80%, 40%-90%, 40%-80%, 50%-90%, 50%-80%, 10%, 20%, 30%, 40%, 50%, 60%, 70%, 75%, 80%, 85%, or 90% of the highest peak for a sample (e.g., in FIG. 2, for PGA-1.1, the peak at about 14.3 min). In some embodiments, a signal detected (e.g., UV absorption at 210 nM, RI detection, etc.) at a time corresponding to the peak elution of a 504,000 Da (e.g., in FIG. 2, the peak at about 13.1 min) standard is about or at least about 10%-95%, 10-90%, 10-80%, 10%-70%, 20%-90%, 20%-80%, 20-70%, 30%-90%, 30%-80%, 40%-90%, 40%-80%, 50%-90%, 50%-80%, 10%, 20%, 30%, 40%, 50%, 60%, 70%, 75%, 80%, 85%, or 90% of the highest peak for a sample (e.g., in FIG. 2, for PGA-1.1, the peak at about 14.3 min). In some embodiments, a signal detected (e.g., UV absorption at 210 nM, RI detection, etc.) at a time corresponding to the peak elution of a 969,000 Da standard (e.g., in FIG. 2, the peak at about 12.3 min) is about or at least about 10%-95%, 10-90%, 10-80%, 10%-70%, 20%-90%, 20%-80%, 20-70%, 30%-90%, 30%-80%, 40%-90%, 40%-80%, 50%-90%, 50%-80%, 10%, 20%, 30%, 40%, 50%, 60%, 70%, 75%, 80%, 85%, or 90% of the highest peak for a sample (e.g., in FIG. 2, for PGA-1.1, the peak at about 14.3 min). In some embodiments, a signal detected (e.g., UV absorption at 210 nM, RI detection, etc.) at any time before the peak elution of a 969,000 standard (e.g., in FIG. 2, the peak at about 12.3 min) is about or at least about 10%-95%, 10-90%, 10-80%, 10%-70%, 20%-90%, 20%-80%, 20-70%, 30%-90%, 30%-80%, 40%-90%, 40%-80%, 50%-90%, 50%-80%, 10%, 20%, 30%, 40%, 50%, 60%, 70%, 75%, 80%, 85%, or 90% of the highest peak for a sample (e.g., in FIG. 2, for PGA-1.1, the peak at about 14.3 min). In some embodiments, a signal detected is from UV, e.g., at 210 nm. In some embodiments, a signal detected is from RI detection, e.g., as shown in FIG. 2. In some embodiments, a percentage is about or at least about 10%. In some embodiments, a percentage is about or at least about 20%. In some embodiments, a percentage is about or at least about 30%. In some embodiments, a percentage is about or at least about 40%. In some embodiments, a percentage is about or at least about 50%. In some embodiments, a percentage is about or at least about 60%. In some embodiments, a percentage is about or at least about 70%. In some embodiments, a percentage is about or at least about 75%. In some embodiments, a percentage is about or at least about 80%. In some embodiments, a percentage is about or at least about 85%. In some embodiments, a percentage is about or at least about 90%.

Certain data for certain batches of PGA are described below (Procedure B, RI)

| PGA Name | $M_p$ (in Million Da) | $M_n$ (in Million Da) | $M_w$ (in Million Da) | Measured PDI |
|---|---|---|---|---|
| PGA-0.02 | N/A | 0.02 | | N/A |
| PGA-0.7 | 0.386 | 0.213M | 0.493 | 2.31 |
| PGA-1.1 | 1.61 | 0.605M | 4.64 | 7.67 |
| PGA-2.0 | 1.68 | 0.646M | 2.21 | 3.42 |

Those skilled in the art reading the present disclosure will appreciate that molecular weight can be measured using other technologies including those described herein, and different methodology may give different molecular weight numbers. In many embodiments, however, regardless of how molecular weight is measured, the general trend remains that an increase in molecular weight will lead to higher viscosity, higher measured molecular weight, and various improved performance properties of γ-PGA absorbent polymers.

Crosslinking 10 g samples of γ-PGA (vendor-provided molecular weight of 700,000 Da to 2,000,000 Da) were added to a 250 mL beaker. It was observed that the higher the molecular weight, the greater the viscosity of solutions at the same mass to volume loading, and solutions of higher molecular weight were made at lower concentrations. For the 2,000,000 Da γ-PGA (PGA-2.0), 90 g of water was added to the beaker to make a 10 wt % solution. 700,000 Da (PGA-0.7) up to 1,000,000 Da (PGA-1.1) γ-PGA were diluted to 20% by adding 40 g of water, and 15 g of water were added to 20,000 Da γ-PGA (PGA-0.02) to make a 40 wt % solution. Mixtures were stirred using an overhead stirrer with a stirring shaft with 6-hole paddle that generates a tangential flow with reduced turbulence and gentle mixing. The mixture was stirred at 400 rpms until the powder went into solution, between 3 to 30 minutes depending on the molecular weight and viscosity of the solution. After mixing, 0.20 g (2 wt %) of sorbitol polyglycidyl ether (Erisys®GE61) was added. The mixture was stirred for an additional 4 minutes at 540-600 rpm. Afterwards the solution was poured into 50 mL shallow aluminum pans and cured in a 150° C. oven for 1.5 hours. After 1.5 hours, all water had evaporated and the mixture had become a thin film on the pan. Upon removal from the oven, 30 to 50 mL of water was added to the pans in order to release the newly formed hydrogel from the aluminum pans. This gel was then placed into an air circulating dehydrating oven at 70° C. for 8-12 hours until it was less than 5% moisture. Alternatively, in some instances, PGA mixtures with crosslinker were poured onto plastic, aluminum foil, teflon or other release designed substrates. Solutions were then crosslinked as mentioned above. In some embodiments, dried materials were removed directly without adding water. This dried hydrogel (SAP) was then ground to small particle size in a mill grinder, sieved between 30, 40, 50 mesh screens in Gaussian distribution, and tested for performance properties. Certain results are presented in Table 2. As demonstrated herein, provided technologies can provide high absorption capacities, and certain technologies, e.g., those comprising relatively high MW PGA, can provide high properties (e.g., AUL values) comparable or better than reference SAPs such as PAA.

TABLE 2

Certain Performance Properties of γ-PGA-based SAP

| PGA | AUL (g/g) | | CRC | Saline Absorption |
| --- | --- | --- | --- | --- |
| | 0.3 psi | 0.7 psi | (g/g) | (g/g) |
| PGA-0.02 | 13.9** | N/A | 32.5** | 52.8** |
| PGA-0.7 | 13.6 (+/−1.6) | N/A | 25.6 (+/−6.9) | 36 (+/−8.1) |
| PGA-1.1 | 25 (+/−3.0) | 19.5 | 25 (+/−3.6) | 32.8 (+/−0.8) |
| PGA-2 | 31 (+/−1.2) | 26.2 | 24.7 (+/−1.8) | 31.94 (+/−4.8) |

**Only one sample. Numbers in parenthesis are standard deviation

As confirmed herein, preparations of the present disclosure can provide compositions with various useful properties including absorption capacities. In some embodiments, AUL is about 10-40, 10-35, 10-30, 10-25, 11-40, 11-35, 11-30, 11-25, 12-40, 12-35, 12-30, 12-25, 15-40, 15-35, 15-30, 15-25, or about or at least about 10, 11, 12, 13, 14, 15, 16, 17, 18, 19, 20, 21, 22, 23, 24, 25, 26, 27, 28, 29 30, 31, 32, 33, 34, 35, 36, 37, 38, 39 or 40 g/g. In some embodiments, AUL is about 10 g/g. In some embodiments, AUL is about 12 g/g. In some embodiments, AUL is about 14 g/g. In some embodiments, AUL is about 15 g/g. In some embodiments, AUL is about 16 g/g. In some embodiments, AUL is about 18 g/g. In some embodiments, AUL is about 20 g/g. In some embodiments, AUL is about 22 g/g. In some embodiments, AUL is about 24 g/g. In some embodiments, AUL is about 25 g/g. In some embodiments, AUL is about 26 g/g. In some embodiments, AUL is about 28 g/g. In some embodiments, AUL is about 30 g/g. In some embodiments, AUL is about 32 g/g. In some embodiments, AUL is about 35 g/g. In some embodiments, an ALU is at 0.3 psi. In some embodiments, an ALU is at 0.7 psi.

Example 2. Various Crosslinking Technologies can be Utilized to Provide SAPs of the Present Disclosure As demonstrated herein, various technologies, including crosslinkers, can be utilized to generate polymers and compositions having desired properties and/or performances for various intended uses such as SAPs in accordance with the present disclosure.

In one set of experiments, it is demonstrated that sorbitol polyglycidyl ether can be utilized under various conditions as crosslinkers.

Compositions were prepared according to Example 1, except the amounts of the crosslinker was varied between 1-10 wt % and the molecular weight of the PGA was 700K Da. Certain results are prepared in Table 3.

TABLE 3

Crosslinker and Certain Performance Properties of γ-PGA-based SAP

| PGA | Crosslinker (wt %) | Saline absorption (% of Control) | CRC (% of Control) | AUL 0.3 psi (g/g) |
| --- | --- | --- | --- | --- |
| PGA-0.7 | 1 | 100% | 100% | TBD |
| PGA-0.7 | 2 | 90% | 83% | TBD |
| PGA-0.7 | 5 | 69% | 79% | TBD |
| PGA-0.7 | 10 | 69% | 72% | TBD |

Other crosslinkers, such as various glycidyl ethers, and/or conditions (e.g., about 90° C. for about 3 hours) can also be utilized, for example, see Table 4 below. Compositions were prepared according to Example 1, except that: A) in addition to sorbitol polyglycidyl ether, butanediol diglycidyl ether (BDDGE), neopentyl glycol diglycidyl ether (NP), Poly (ethylene glycol) diglycidyl ether (PEGGE; e.g., mw=500), Ethylene Glycol Diglycidyl Ether (EDGE), Poly(propylene glycol) diglycidyl ether (PPGGE; e.g., mw=640 Da), Trimethylolpropane triglycidyl ether (TMPTGE), Erisys® GE-60, and Glycerol diglycidyl ether (GLGE) were also assessed as crosslinkers. B) Concentration of a few of the crosslinker was varied between about 1 and 10 mol %. Certain results are presented in Table 4. In some embodiments, two or more crosslinker are utilized.

TABLE 4

Crosslinker and Certain Performance Properties of γ-PGA-based SAP

| Number | PGA | Crosslinker Mol % | Crosslinker | CRC g/g | AUL 0.3 psi g/g |
| --- | --- | --- | --- | --- | --- |
| AF019 | PGA-1.1 | 1 | BDDGE | 31.0 | 9.8 |
| AF020 | PGA-1.1 | 4 | BDDGE | 29.6 | 9.1 |
| AF021 | PGA-1.1 | 7 | BDDGE | 25.5 | 10.2 |
| AF022 | PGA-1.1 | 10 | BDDGE | 21.8 | 14.4 |
| AF001 | PGA-1.1 | 1 | NP | 36.5 | 8.3 |
| AF002 | PGA-1.1 | 4 | NP | 19.0 | 15.7 |
| AF003 | PGA-1.1 | 7 | NP | 18.0 | 20.2 |
| AF004 | PGA-1.1 | 10 | NP | 16.0 | 17.3 |
| JP-57A | PGA-1.1 | 3* | Erisys ® GE-61 | 28.5 | 14.6** |
| JP-57B | PGA-1.1 | 3* | TMPTGE | 27.1 | 13.0** |
| AF105 | PGA-0.7 | 0.5* | Erisys ® GE-60 | 30 | 12** |
| HG113 | PGA-2.0 | 5* | EDGE | 28 | 12 |
| JP-101 | PGA-2.0 | 1* | PPGGE | 52 | 2** |
| HG112 | PGA-2.0 | 5* | PEGGE | 32 | 15 |
| HG109 | PGA-2.0 | 5* | GLGE | 27 | 20 |
| JP-59 | PGA-2.0 | 0.5* | Erisys ® GE-61 | 45.3 | 9.9** |
| JP-52A | PGA-2.0 | 1* | Erisys ® GE-61 | 35.7 | 11.3** |
| JP-56D | PGA-2.0 | 2* | Erisys ® GE-61 | 34.6 | 10.6** |
| JP-57A | PGA-2.0 | 3* | Erisys ® GE-61 | 28.5 | 14.6** |

BDDGE is butanediol diglycidyl ether.
Erisys ® GE-61 and GE-60 are a multifunctional sorbitol glycidyl ether.
NP is neopentylglycol diglycidyl ether.
TMPTGE is Trimethylolpropane triglycidyl ether.
PEGGE is Poly(ethylene glycol) diglycidyl ether (mw = 500).
EDGE is Ethylene Glycol Diglycidyl Ether.
PPGGE is Poly(propylene glycol) diglycidyl ether (mw = 640 Da).
GLGE is Glycerol diglycidyl ether.
**AUL measured at 0.7 psi.
*Crosslinker concentration in weight %.

BDDGE is butanediol diglycidyl ether. Erisys® GE-61 and GE-60 are a multifunctional sorbitol glycidyl ether. NP is neopentylglycol diglycidyl ether. TMPTGE is Trimethylolpropane triglycidyl ether. PEGGE is Poly(ethylene glycol) diglycidyl ether (mw=500). EDGE is Ethylene Glycol Diglycidyl Ether. PPGGE is Poly(propylene glycol) diglycidyl ether (mw=640 Da). GLGE is Glycerol diglycidyl ether. ** AUL measured at 0.7 psi. * Crosslinker concentration in weight %.

As demonstrated in Table 5 below, various sorbitol polyglycidyl ethers and various conditions can be utilized to provide polymers and compositions in accordance with the present disclosure. Compositions were prepared according to Example 1, except a more water soluble sorbitol polyglycidyl ether was used as a crosslinker (SorbGE). The incubation was carried out at both 90° C. for 12 hours and 150° C. for 1.5 hours and MW of the PGA was 700 KDa. Certain results are presented in Table 6.

TABLE 5

Crosslinking conditions and certain performance properties of γ-PGA-based SAP

| Number | Formulation | Cure Temp ° C. | CRC g/g | AUL 0.3 psi g/g |
|---|---|---|---|---|
| AF086 | PGA-0.7/2 wt % Erisys ® GE-61 | 90 | 20.7 | 9.2 |
| AF086 | PGA-0.7/2 wt % Erisys ® GE-61 | 150 | 23.1 | N/D |
| AF087 | PGA-0.7/2 wt % Erisys ® GE-61 | 90 | 26.5 | 9.8 |
| AF087 | PGA-0.7/2 wt % Erisys ® GE-61 | 150 | 29.2 | N/D |
| AF089 | PGA-0.7/2 wt % Erisys ® GE-61 | 90 | 28.8 | 10.7 |
| AF089 | PGA-0.7/2 wt % Erisys ® GE-61 | 150 | 26.9 | 11.1 |
| AF091 | PGA-0.7/2 wt % Erisys ® GE-61 | 90 | 33.2 | 8.2 |
| AF091 | PGA-0.7/2 wt % Erisys ® GE-61 | 150 | 31.9 | 11.2 |

TABLE 6

Crosslinking conditions and certain performance properties of γ-PGA-based SAP using PGA-2.0 and 2 wt. % Erisys ® GE-61 at different times and temperatures

| ID Number | Cure Temp (° C.) | Time (hours) | CRC (g/g) | AUL 0.7 psi (g/g) |
|---|---|---|---|---|
| JP-2 | 150 | 2 | 31.75 | 17.3 |
| JP-12(9) | 150 | 7 | 24.1 | 8.19 |
| JP-2 | 120 | 7 | 23.1 | 17.3 |
| AP-47 | 90 | 17 | 28.2 | 17.0 |
| JP-47A | 60 | 17 | 30.0 | 14.3 |

Example 3. Surface Crosslinked Particles May Provide Improvements

Among other things, the present disclosure provides technologies comprising surface crosslinked particles, which particles may comprise or consist essentially of crosslinked polymers. In some embodiments, further surface crosslinking may provide improved properties and/or performances as demonstrated herein.

In a preparation (3A), 2.5 g of bulk crosslinked (see example 1 for protocol) PGA (700,000 Da) were added to a small coffee grinder. 1 mL of an ethanol solution of sorbitol polyglycidyl ether (0.01 molar in ethanol) is pipetted onto the SAP in the grinder. The mixture is then pulsed 5-10 times and then transferred to a small shallow aluminum pan and placed into a 150° C. oven for 15 minutes. After 15 minutes the pans are removed from the oven, the SAP material cooled to room temperature, reground to remove aggregates and tested for performance. Certain results are presented in Table 7.

In another preparation (3B), 5 g of bulk crosslinked (see example 1 for protocol) PGA (700,000 Da) were added to a small coffee grinder, whereby 0.01 to 1 mol % sorbitol-polyglycidyl ether in 500 uL of water are added. The mixture is pulse mixed 5-10 times and then transferred onto an aluminum pan and cured at 150° C. for 30 minutes. Once cooled, the surface crosslinked polymer was ground and sieved as before and performance properties measured. Certain results are presented in Table 5.

In yet another preparation (3C), 5 g of bulk crosslinked (see example 1 for protocol) PGA-0.7 were added to a small coffee grinder, whereby 0.01-1 mol % allyl glycidyl ether, 0.05 mol V-044 azo initiator from Fuji Film Wako Specialty Chemicals, dissolved into 500 uL of water are added. The mixture is pulse mixed 5-10 times and then transferred onto an aluminum pan and cured at 150° C. for 30 minutes. Once cooled, the surface crosslinked polymer was ground and sieved as before and properties measured. Certain results are presented in Table 6.

TABLE 7

Surface Crosslinking and Certain Performance Properties of γ-PGA-based SAP

| Number | Surface treatment | CRC g/g (Base Poly) | CRC g/g (Surface Treated) | AUL 0.3 psi g/g (Base Poly) | AUL 0.3 psi g/g (Surface Treated) |
|---|---|---|---|---|---|
| 3A | Erisys ® GE61 | 31 | 13.3 | 10.3 | 17.6 |
| 3B | Erisys ® GE61 | 31 | 10.6 | 10.6 | 20.8 |
| 3C | Allyl glycidyl ether | 31 | 13.8 | 13.8 | 21.9 |

Example 4. Compositions Crosslinked by Radiation

In some embodiments, provided polymers are crosslinked by radiation. In some embodiments, polymers are crosslinked by e-beam irradiation. In some embodiments, γ-PGAs of different molecular weights were crosslinked by first put into solution and then irradiated with a total dosage of 100 KGy. First, 20 mL of water solutions of different molecular weight γ-PGA were added to 20 mL scintillation vials. Solutions from 5 wt %-20 wt % were prepared. The vials were placed in a box and run through an electron beam accelerator tunnel whose speed was calculated to administer a total dosage of 100 kGy. Gels were removed from vials, dried, ground to a Gaussian mesh size distribution between 30-60 mesh, and tested for CRC and AUL (0.3 psi). Table 8 presents certain data. As observed, at least in some embodiments, higher molecular weight polymers may provide higher AUL.

TABLE 8

E-Beam Crosslinking and Certain Performance Properties of γ-PGA-based SAP

| PGA Mw Da | Solution % | CRC (g/g) | AUL 0.3 psi g/g |
|---|---|---|---|
| PGA-0.020 | 20 | 38 | 8.4 |
| PGA-2.0 | 10 | 47 | 11.4 |
| PGA-2.0 | 5 | 41 | 14.1 |

In some embodiments, 10 grams of PGA was dissolved into 100 grams of water and solutions were subjected to E-beam at different energy values. Table 9 presents certain data. As observed, at least in some embodiments, high e-beam energy may provide increased AUL and CRC values.

TABLE 9

E-Beam Crosslinking and Certain Performance Properties of PGA-2.0 based γ-PGA-based SAP at different energy levels.

| E-Beam (kGy) | CRC (g/g) | AUL 0.3 psi g/g |
|---|---|---|
| 30 | 20.4 | 7.5 |
| 45 | 35.7 | 7.7 |
| 60 | 62.2 | 8.6 |
| 75 | 48.2 | 9.5 |

TABLE 9-continued

E-Beam Crosslinking and Certain Performance Properties of
PGA-2.0 based γ-PGA-based SAP at different energy levels.

| E-Beam (kGy) | CRC (g/g) | AUL 0.3 psi g/g |
|---|---|---|
| 90 | 53.0 | 9.0 |
| 105 | 49.1 | 10.4 |

Example 5. Vortex Test

In some embodiments, vortex test was run according to the previous section on "Vortex method (absorption speed)". PGA based SAP (JP-56D, from Table 4) and was determined to be 60 seconds. SAP (JP-52A, from table 4) was determined to be 36 seconds.

Example 6. The Present Disclosure Provides Biodegradable Polymer Compositions

Among other things, the present disclosure provides polymers, compositions, and products therefrom that are biodegradable and environmentally friendly. In some embodiments, biodegradation, e.g., based on carbon to carbon dioxide conversion for solid materials (Sturm test), may be performed according to OECD 301B. In some embodiments, a test determines an aquatic, aerobic biodegradation of a solid sample under laboratory conditions and is predictive of the biodegradability of a material in surface waters or an aerobic waste water treatment plant. In some embodiments, a test material is brought into a chemically defined (mineral) liquid medium, essentially free of other organic carbon sources, and spiked with micro-organisms (activated sludge). In some embodiments, during an aerobic biodegradation of organic materials in an aqueous medium, oxygen is consumed and carbon is converted to gaseous, mineral C (under the form of carbon dioxide, $CO_2$). In some embodiments, part of the organic material is assimilated for cell growth. Typically, reactors are continuously aerated while exhaust air is led through caustic solution to absorb all $CO_2$ produced. In some embodiments, the amount of $CO_2$ produced is determined by titration and used to calculate the percentage of biodegradation.

Another useful way to determine biodegradation potential utilizes a simple plate assay, in which polymer-degrading activity is detected based on either the formation of a clear zone surrounding fungal colonies or the growth of bacterial isolates as clear colonies on media with the polymer as a sole carbon source. Useful microbes include *P. aeruginosa* and *T. rubrum* colonies.

Various technologies are available for assess degradability of provided compositions and preparations in accordance with the present disclosure. Certain such technologies and/or protocols are listed below:

| | |
|---|---|
| Aquatic Aerobic Biodegradation | OECD 301A, OECD 301B, OECD 301C, OECD 301D, OECD 301E, OECD 301F, ASTM D5210, ASTM D5988, OECD 311, OECD 302B, ASTM D5511, ASTM D5864, ASTM D5271, OECD 310, ISO 14593 |
| Aerobic Biodegradation | ISO 14855, ASTM D5338, ISO 14852, ASTM 6868 |
| Oxobiodegradation & Biodegradation | ASTM D6954 |
| Compostability | ASTM D6400, ISO 16929, ISO14855 |
| Anaerobic Biodegradability | ISO 15985 |

Figure 3:
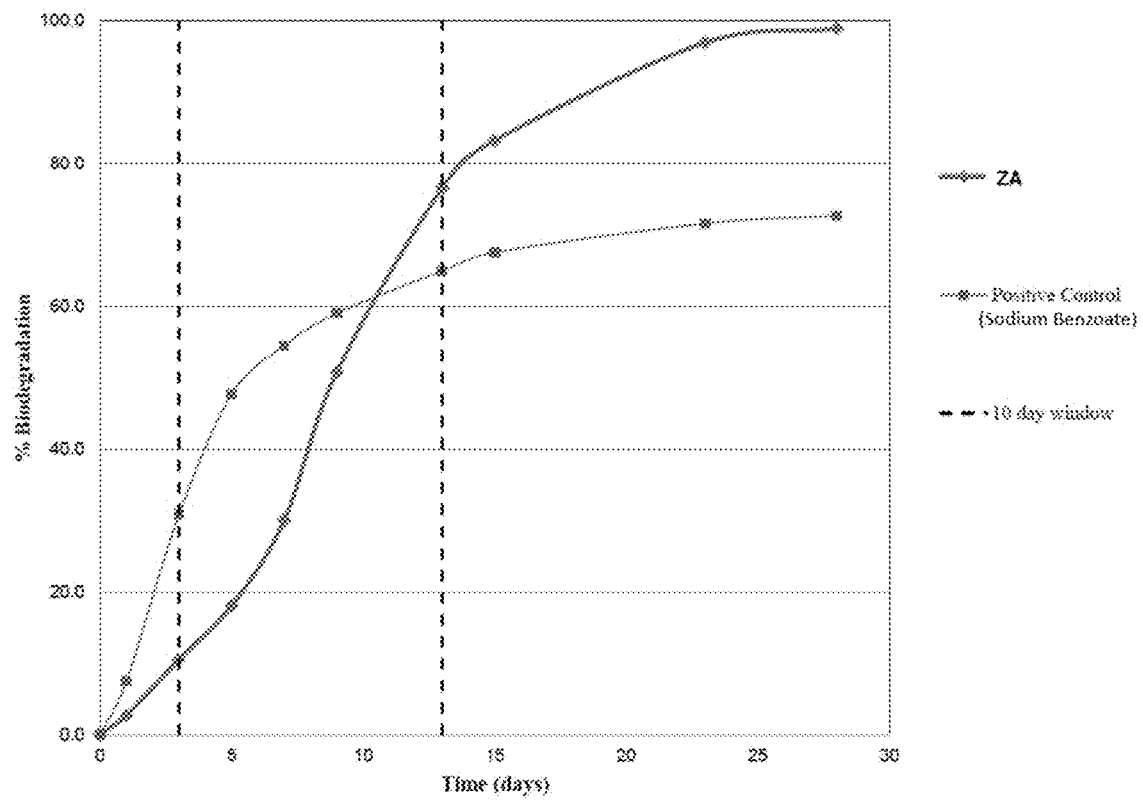
FIG. 3. Certain biodegradation data.

In some embodiments, the present disclosure provides compositions, preparations, products, etc. that are degradable per one or more such technologies/protocols, e.g., OECD 301B. In some embodiments, degradation is biodegradation. In some embodiments, degradation is assessed according to OECD 301B. In some embodiments, degradation is comparable or faster than a positive control. In some embodiments, degradation levels after periods of time (e.g., at about or after about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, 1, 2, 3, 4, 5, 6, 7, 8, 9, 10, 11 or 12 months, 1, 2, 3, 4, 5, 6, 7, 8, 9, or 10 years etc.) are at comparable, about the same, or higher levels than one or more positive controls (e.g., sodium benzoate). In some embodiments, a period of time is about 5 days. In some embodiments, a period of time is about 7 days. In some embodiments, a period of time is about 10 days. In some embodiments, a period of time is about 15 days. In some embodiments, a period of time is about 20 days. In some embodiments, a period of time is about 25 days. In some embodiments, a period of time is about 30 days. In some embodiments, a level is about or at least about 10%-100%, 10%-95%, 10-90%, 10-80%, 10%-70%, 20%-90%, 20%-80%, 20-70%, 30%-90%, 30%-80%, 40%-90%, 40%-80%, 50%-90%, 50%-80%, 10%, 20%, 30%, 40%, 50%, 60%, 70%, 75%, 80%, 85%, 90%, 95%, 98%, or 100%. In some embodiments, a level is about or at least about 10%. In some embodiments, a level is about or at least about 20%. In some embodiments, a level is about or at least about 30%. In some embodiments, a level is about or at least about 40%. In some embodiments, a level is about or at least about 50%. In some embodiments, a level is about or at least about 60%. In some embodiments, a level is about or at least about 70%. In some embodiments, a level is about or at least about 75%. In some embodiments, a level is about or at least about 80%. In some embodiments, a level is about or at least about 85%. In some embodiments, a level is about or at least about 90%. In some embodiments, a level is about or at least about 95%. In some embodiments, a level is about or at least about 98%. In some embodiments, a level is about or at least about 100%. In some embodiments, time consumed to degrade a certain level (e.g., 10%, 20%, 30%, 40%, 50%, 60%, 70%, 80%, 90%, etc.) of a composition, preparation or product is no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days. In some embodiments, it is no more than about 5 days. In some embodiments, it is no more than about 7 days. In some embodiments, it is no more than about 10 days. In some embodiments, it is no more than about 15 days. In some embodiments, it is no more than about 20 days. In some embodiments, it is no more than about 25 days. In some embodiments, it is no more than about 30 days. In some embodiments, time consumed to degrade a certain level (e.g., 10%, 20%, 30%, 40%, 50%, 60%, 70%, 80%, 90%, etc.) of a composition, preparation or product is shorter, about the same or no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days longer than time consumed to degrade the same level of a positive control under a comparable condition. In some embodiments, it is no more than about 5 days. In some embodiments, it is no more than about 7 days. In some embodiments, it is no more than about 10 days. In some embodiments, it is no more than about 15 days. In some embodiments, it is no more than about 20 days. In some embodiments, it is no more than about 25 days. In some embodiments, it is no more than about 30 days. In some embodiments, a level is 50%. In some embodiments, biodegradability was assessed using OECD 301B $CO_2$ evolution test. In some embodiments, an assessment monitors degree of activity of microorganisms exposed to a material that is being assessed for a biodegradable status. In some embodiments, if microorganisms recognize a material as a food source, then an increase in biological activity is observed through data collection specifically designed to assess biological conversion of organic carbon to inorganic carbon (i.e. $CO_2$). In some embodiments, if a material is not a recognizable food source or is toxic or inhibitory, then there is no measurable increase in biological activity or, in some cases, there is a marked decrease in activity relative to a biodegradable control. In one assessment, a crosslinked γ-PGA composition prepared using technologies described herein (ZA in FIG. 3) was evaluated for biodegradability in an aqueous medium when exposed to an inoculum source collected from the Escatawpa, Mississippi POTW according to the procedures detailed in the OECD 301B methodology. Based on a testing conducted in accordance with OECD301B methodologies, 98.8% biodegradation was achieved in less than 30 days (See FIG. 3). In some embodiments, provided preparations, compositions and products satisfies Ready Biodegradability testing classification.

The invention claimed is:

1. A composition, comprising a number of γ-polyglutamic acid (PGA) molecules crosslinked with a crosslinker, wherein:

each γ-polyglutamic acid molecule independently has a structure of:

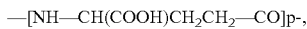
—[NH—CH(COOH)CH$_2$CH$_2$—CO]p-, wherein each p is at least about 1000;
the composition is enriched from PGA molecules for which p is about 2000 to about 10000; and
the crosslinker is sorbitol polyglycidyl ether, wherein the amount of the crosslinker is about 1-3% of the total weight of γ-polyglutamic acid and sorbitol polyglycidyl ether in the composition.

2. The composition of claim 1, wherein p is at least about 2000 for at least about 50% (mol %) of PGA molecules in the composition.

3. The composition of claim 1, wherein p is at least about 2000 for at least about 60% (mol %) of PGA molecules in the composition.

4. The composition of claim 1, wherein p is at least about 2000 for at least about 70% (mol %) of PGA molecules in the composition.

5. The composition of claim 1, wherein p is at least about 2000 for at least about 80% (mol %) of PGA molecules in the composition.

6. The composition of claim 1, wherein p is at least about 2000 for at least about 90% (mol %) of PGA molecules in the composition.

7. The composition of claim 1, wherein p is about 2000 to about 1000 for at least about 30% (mol %) of PGA molecules in the composition.

8. The composition of claim 1, wherein p is about 2000 to about 1000 for at least about 40% (mol %) of PGA molecules in the composition.

9. The composition of claim 1, wherein p is about 2000 to about 1000 for at least about 50% (mol %) of PGA molecules in the composition.

10. The composition of claim 1, wherein p is about 2000 to about 1000 for at least about 60% (mol %) of PGA molecules in the composition.

11. The composition of claim 1, wherein p is about 2000 to about 1000 for at least about 70% (mol %) of PGA molecules in the composition.

12. The composition of claim 1, wherein the average of p for PGA molecules in the composition is about 5000.

13. The composition of claim 1, wherein the composition has an absorption under load (AUL) of about 10 to 50 g/g under 0.7 psi when assessed according to ISO 17190-7.

14. The composition of claim 1, wherein the composition has an absorption under load (AUL) of about 15 to 40 g/g under 0.7 psi when assessed according to ISO 17190-7.

15. The composition of claim 1, wherein the composition has a centrifugal retention capacity (CRC) of about 20 to 50 g/g when assessed according to ISO 17190-6.

16. The composition of claim 1, wherein the composition has a centrifugal retention capacity (CRC) of about 25-40 g/g when assessed according to ISO 17190-6.

17. The composition of claim 12, wherein the composition has an absorption under load (AUL) of about 15 to 40 g/g under 0.7 psi when assessed according to ISO 17190-7, and a centrifugal retention capacity (CRC) of about 20-40 g/g when assessed according to ISO 17190-6.

18. An article comprising a composition of claim 1.

19. A method, comprising contacting a liquid with a composition of claim 1, wherein the composition or article absorbs the liquid.

20. A method, comprising contacting a liquid with an article of claim 18, wherein the composition or article absorbs the liquid.

* * * * *